United States Patent [19]

Bartmann et al.

[11] Patent Number: 5,571,449
[45] Date of Patent: Nov. 5, 1996

[54] PARTIALLY FLUORINATED BENZENE DERIVATIVES

[75] Inventors: Ekkehard Bartmann, Erzhausen; Herbert Plach, Darmstadt; Rudolf Eidenschink, Mainz, all of Germany

[73] Assignee: Merck Patent Gesellschaft mit beschrankter Haftung, Darmstadt, Germany

[21] Appl. No.: 373,283

[22] PCT Filed: May 9, 1994

[86] PCT No.: PCT/EP94/01487

§ 371 Date: Jan. 19, 1995

§ 102(e) Date: Jan. 19, 1995

[87] PCT Pub. No.: WO94/26839

PCT Pub. Date: Nov. 24, 1994

[30] Foreign Application Priority Data

May 19, 1993 [DE] Germany ............ 43 16 909.0

[51] Int. Cl.$^6$ ............ C09K 19/06; C09K 19/30; C09K 19/12; C07C 22/00
[52] U.S. Cl. ............ 252/299.6; 252/299.61; 252/299.62; 252/299.63; 252/299.65; 252/299.66; 252/299.67; 570/129; 570/144; 568/647; 560/63; 560/102; 560/108; 544/224; 544/298; 546/339
[58] Field of Search ............ 252/299.63, 299.66, 252/299.6, 299.62, 299.61, 299.65, 299.67; 570/144; 560/63, 102, 108; 568/647; 546/339; 544/224, 298

[56] References Cited

U.S. PATENT DOCUMENTS

| | | | |
|---|---|---|---|
| 5,190,688 | 3/1993 | Sage et al. | 252/299.01 |
| 5,198,151 | 3/1993 | Kuratate et al. | 252/299.66 |
| 5,262,082 | 11/1993 | Janulis et al. | 252/299.01 |
| 5,308,537 | 5/1994 | Coates et al. | 252/299.6 |

FOREIGN PATENT DOCUMENTS 4219819 12/1993 Germany.

*Primary Examiner*—C. H. Kelly
*Attorney, Agent, or Firm*—Millen, White, Zelano & Branigan, P.C.

[57] ABSTRACT

Partially fluorinated benzene derivatives of the formula I

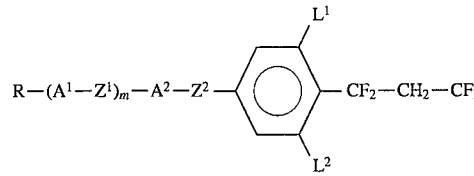

in which
R, $A^1$, $A^2$, $Z^1$, $Z^2$, $L^1$, $L^2$ and m are as defined in claim 1, are suitable as components of liquid-crystalline media.

18 Claims, No Drawings

PARTIALLY FLUORINATED BENZENE DERIVATIVES

The invention relates to partially fluorinated benzene derivatives of the formula I

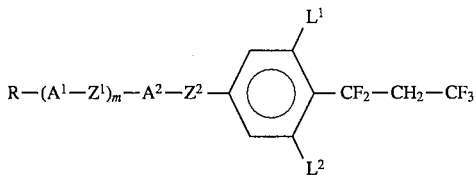

where

R is H, an alkyl or alkenyl radical having 1 to 15 carbon atoms which is unsubstituted or monosubstituted by CN or $CF_3$ or at least monosubstituted by halogen, it also being possible for one or more $CH_2$ groups in these radicals to be replaced, in each case independently of one another, by —O—, —S—,

—CO—, —CO—O—, —O—CO— or —O—CO—O— in such a manner that O atoms are not linked directly to one another, $A^1$ and $A^2$ are each, independently of one another, a
  (a) trans-1,4-cyclohexylene radical in which, in addition, one or more nonadjacent $CH_2$ groups may be replaced by —O— and/or —S—,
  (b) 1,4-phenylene radical in which, in addition, one or two CH groups may be replaced by N,
  (c) radical from the group consisting of 1,4-cyclohexenylene, 1,4-bicyclo-(2,2,2)octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by one or two fluorine atoms, $Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, and one of the radicals $Z^1$ and $Z^2$ is alternatively —$(CH_2)_4$— or —CH=CH—$CH_2CH_2$—, and m is 0, 1 or 2, $L^1$ and $L^2$ are each, independently of one another, H or F.

The invention furthermore relates to the use of these compounds as components of liquid-crystalline media, and to liquid-crystal and electrooptical display elements which contain the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The invention had the object of finding novel, stable liquid-crystalline or mesogenic compounds which are suitable as components of liquid-crystalline media and in particular have at the same time comparatively low viscosity and relatively high dielectric anisotropy.

It has now been found that compounds of the formula I are eminently suitable as components of liquid-crystalline media. In particular, they have comparatively low viscosities. They can be used to obtain stable liquid-crystalline media which have a broad mesophase range and advantageous values for the optical and dielectric anisotropy. These media furthermore have very good low-temperature behavior.

The general formula in WO-00335 covers the novel compounds, but they are not mentioned explicitly.

Similar fluorinated compounds are described in DE-A 41 01 600 and DE-A 40 02 374.

In view of the extremely wide variety of areas of application of such compounds of high Δε, however, it was desirable to have further compounds of high nematogeneity available which have properties precisely tailored to the particular application.

In addition, the provision of the compounds of the formula I very generally considerably broadens the range of liquid-crystalline substances which are suitable, from various applicational points of view, for the preparation of liquid-crystalline mixtures.

The compounds of the formula I have a broad field of application. Depending on the choice of substituents, these compounds can be used as base materials from which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or viscosity.

In the pure state, the compounds of the formula I are colorless and formliquid-crystalline mesophases in a temperature range which is favorably located for electrooptical use. They are stable chemically, thermally and to light.

The invention thus relates to the compounds of the formula I and to the use of these compounds as components of liquid-crystalline media. The invention furthermore relates to liquid-crystalline media containing at least one compound of the formula I, and to liquid-crystal display elements, in particular electrooptical display elements, which contain media of this type.

For reasons of simplicity below, $A^3$ is a radical of the formula

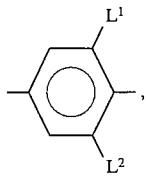

Y is $CF_2$—$CH_2$—$CF_3$, Cyc is a 1,4-cyclohexylene radical, Che is a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)octylene radical, it being possible for Cyc and/or Phe to be unsubstituted or monosubstituted or disubstituted by F or CN.

$A^1$ and $A^2$ are preferably selected from the group consisting of Cyc, Che, Phe, Pyr, Pyd and Dio, it being preferred for only one of the radicals $A^1$ and $A^2$ present in the molecule to be Che, Phe, Pyr, Pyd or Dio.

Accordingly, the compounds of the formula I cover bicyclic compounds of the subformulae Ia to Ib:

R—$A^2$—$A^3$—Y      Ia

R—$A^2$—$Z^2$—$A^3$—Y      Ib tricyclic compounds of the subformulae Ic to If:

R—$A^1$—$A^2$—$A^3$—Y      Ic

R—A¹—Z¹—A²—Z²—A³—Y  Id

R—A¹—Z¹—A²—A³—Y  Ie

R—A¹—A²—Z²—A³—Y  If and tetracyclic compounds of the subformulae Ig to Im:

R—A¹—A¹—A²—A³—Y  Ig

R—A¹—Z¹—A¹—A²—A³—Y  Ih

R—A¹—A¹—Z¹—A²—A³—Y  Ii

R—A¹—A¹—A²—Z²—A³—Y  Ij

R—A¹—Z¹—A¹—Z¹—A²—A³—Y  Ik

R—A¹—A¹—Z¹—A²—Z²—A³—Y  Il

R—A¹—Z¹—A¹—Z¹—A²—Z²—A³—Y  Im

Of these, those of the subformulae Ia, Ib, Ic, Id, Ie, If, Ii and Il are particularly preferred.

The preferred compounds of the subformula Ia are those of the subformulae Iaa to Iaf:

R—Phe—A³—Y  Iaa

R—Dio—A³—Y  Iab

R—Pyr—A³—Y  Iac

R—Pyd—A³—Y  Iad

R—Cyc—A³—Y  Iae

R—Che—A³—Y  Iaf

Of these, those of the formulae Iaa and Iae are particularly preferred.

The preferred compounds of the subformula Ib are those of the subformulae Iba to Ibc:

R—Cyc—CH₂CH₂—A³—Y  Iba

R—Cyc—COO—A³—Y  Ibb

R—Phe—COO—A³—Y  Ibc

The preferred compounds of the subformula Ic are those of the subformulae Ica to Icn:

R—Phe—Phe—A³—Y  Ica

R—Phe—Pyd—A³—Y  Icb

R—Phe—Dio—A³—Y  Icc

R—Cyc—Cyc—A³—Y  Icd

R—Phe—Cyc—A³—Y  Ice

R—Cyc—Pyd—A³—Y  Icf

R—Pyd—Phe—A³—Y  Icg

R—Pyr—Phe—A³—Y  Ich

R—Phe—Pyr—A³—Y  Ici

R—Cyc—Pyr—A³—Y  Icj

R—Cyc—Phe—A³—Y  Ick

R—Dio—Phe—A³—Y  Icl

R—Che—Phe—A³—Y  Icm

R—Phe—Che—A³—Y  Icn

Of these, those of the formulae Ica, Icd, Ice and Ick are particularly preferred.

The preferred compounds of the subformula Id are those of the subformulae Ida to Idk:

R—Phe—Z¹—Phe—Z²—A³—Y  Ida

R—Phe—Z¹—Dio—Z²—A³—Y  Idb

R—Cyc—Z¹—Cyc—Z²—A³—Y  Idc

R—Cyc—Z¹—Pyr—Z²—A³—Y  Idd

R—Pyd—Z¹—Phe—Z²—A³—Y  Ide

R—Phe—Z¹—Pyd—Z²—A³—Y  Idf

R—Pyr—Z¹—Phe—Z²—A³—Y  Idg

R—Phe—Z¹—Pyr—Z²—A³—Y  Idh

R—Phe—Z¹—Cyc—Z²—A³—Y  Idi

R—Cyc—Z¹—Phe—Z²—A³—Y  Idj

R—Dio—Z¹—Phe—Z²—A³—Y  Idk

The preferred compounds of the subformula Ie are those of the subformulae Iea to Iej:

R—Pyr—Z¹—Phe—A³—Y  Iea

R—Dio—Z¹—Phe—A³—Y  Ieb

R—Phe—Z¹—Phe—A³—Y  Iec

R—Cyc—Z¹—Phe—A³—Y  Ied

R—Phe—Z¹—Cyc—A³—Y  Iee

R—Cyc—Z¹—Cyc—A³—Y  Ief

R—Phe—Z¹—Dio—A³—Y  Ieg

R—Pyd—Z¹—Phe—A³—Y  Ieh

R—Phe—Z¹—Pyr—A³—Y  Iei

R—Cyc—Z¹—Pyr—A³—Y  Iej

The preferred compounds of the subformula If are those of the subformulae Ifa to Ifn R—Pyr—Phe—Z²—A³—Y  Ifa R—Pyr—Phe—OCH₂—A³—Y  Ifb R—Phe—Phe—Z²—A³—Y  Ifc R—Phe—Phe—OOC—A³—Y  Ifd R—Cyc—Cyc—Z²—A³—Y  Ife R—Cyc—Cyc—CH₂CH₂—A³—Y  Iff R—Pyd—Phe—Z²—A³—Y  Ifg R—Dio—Phe—Z²—A³—Y  Ifh R—Phe—Cyc—Z²—A³—Y  Ifi R—Phe—Pyd—Z²—A³—Y  Ifj R—Che—Phe—Z²—A³—Y  Ifk R—Phe—Che—Z²—A³—Y  Ifl R—Cyc—Phe—Z²—A³—Y  Ifm R—Cyc—Phe—OOC—A³—Y  Ifn Preference is also given to compounds of the formula I and all subformulae in which $A^1$ and $A^2$ are 1,4-phenylene which is monosubstituted or disubstituted by F or monosubstituted by CN. These are, in particular, 2-fluoro-1,4-phenylene, 3-fluoro-1,4-phenylene and 3,5-difluoro-1,4-phenylene, and 2-cyano-1,4-phenylene and 3-cyano-1,4-phenylene. In a particularly preferred embodiment, $A^2$ is 3,5-difluoro-1,4-phenylene, and m is 1 or 2.

$A^3$ is preferably

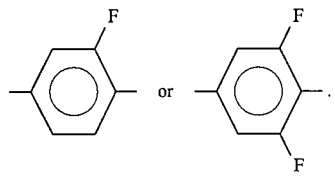

$Z^1$ and $Z^2$ are preferably a single bond, —CO—O—, —O—CO— and —CH₂CH₂—, and secondarily preferably —CH₂O— and —OCH₂—.

If one of the radicals $Z^1$ and $Z^2$ is —(CH₂)₄— or —CH=CH—CH₂CH₂—, the other radical $Z^1$ or $Z^2$ (if present) is preferably a single bond.

Preferred compounds of this type conform to the subformula I'

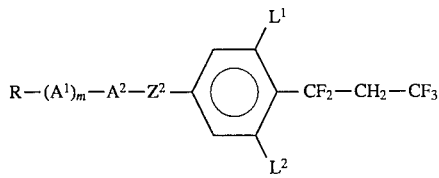

in which $Z^2$ is —(CH₂)₄— or —CH=CH—CH₂CH₂—, and R, $A^1$, $A^2$, $L^1$, $L^2$ and m are as defined under formula I. The preferred meanings for R, $A^1$, $A^2$ and m also correspond to those for the compounds of the formula I.

m is preferably 1 or 0, particularly preferably 1.

If R is an alkyl radical and/or an alkoxy radical, this may be straight-chain or branched. It is preferably straight-chain, has 2, 3, 4, 5, 6 or 7 carbon atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

If R is an alkyl radical in which one CH₂ group has been replaced by —CH=CH—, this may be straight-chain or branched. It is preferably straight-chain and has 2 to 10 carbon atoms. It is accordingly particularly vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, or dec-1-, 2-, 3-, 4-, 5-, 6-, 7-, 8- or dec-9-enyl.

If R is an alkyl radical in which one CH₂ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

They are accordingly particularly acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl 2-(propoxycarbonyl)ethyl, 3-(methoxycarbonyl)propyl, 3-(ethoxycarbonyl)propyl or 4-(methoxycarbonyl)butyl.

If R is an alkyl radical in which one CH₂ group has been replaced by unsubstituted or substituted —CH=CH— and an adjacent CH₂ group has been replaced by CO or CO—O or O—CO—, this may be straight-chain or branched. It is preferably straight-chain and has 4 to 13 carbon atoms. It is accordingly particularly acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or CF₃, this radical is preferably straight-chain and the substitution is by CN or CF₃ in the ω-position.

If R is an alkyl or alkenyl radical which is at least monosubstituted by halogen, this radical is preferably straight-chain and halogen is preferably F or Cl. In the case of multiple substitution, halogen is preferably F. The resulting radicals also include perfluorinated radicals. In the case of monosubstitution, the fluorine or chlorine substituent can be in any desired position, but is preferably in the ω-position.

Compounds of the formula I which contain wing groups R which are suitable for polymerization reactions are suitable for the preparation of liquid-crystalline polymers.

Compounds of the formula I containing branched wing groups R may occasionally be of importance due to better solubility in customary liquid-crystalline base materials, but in particular as chiral dopes if they are optically active. Smectic compounds of this type are suitable as components for ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2 -methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more CH₂ groups have been replaced by —O— and/or —CO—O—, this may be straight-chain or branched. It is preferably branched and has 3 to 12 carbon atoms. It is accordingly particularly biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl) ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl) methyl, 2,2-bis(ethoxycarbonyl)ethyl, 3,3-bis(ethoxycarbonyl) propyl, 4,4-bis(ethoxycarbonyl)butyl or 5,5-bis(ethoxycarbonyl)hexyl.

Compounds of the formula I which contain wing groups R which are suitable for polycondensations are suitable for the preparation of liquid-crystalline polycondensates.

Formula I covers the racemates of these compounds and the optical antipodes, and mixtures thereof.

Of these compounds of the formula I and the subformulae, those are preferred in which at least one of the radicals present therein has one of the preferred meanings indicated.

In the compounds of the formula I, those stereoisomers in which the rings Cyc and piperidine are trans-1,4-disubstituted are preferred. Those of the abovementioned formulae which contain one or more groups Pyd, Pyr and/or Dio in each case cover the two 2,5-positional isomers.

Preferred smaller groups of compounds are those of the subformulae I1 to I30:

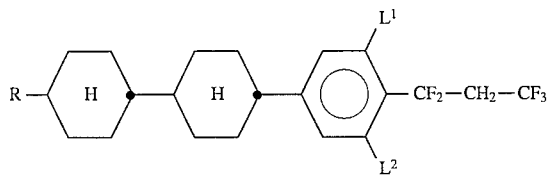

I1

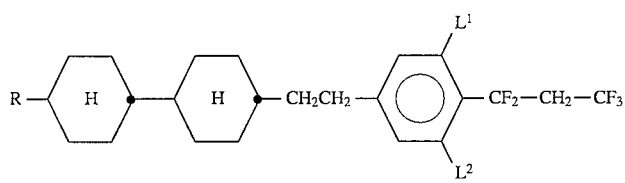

I2

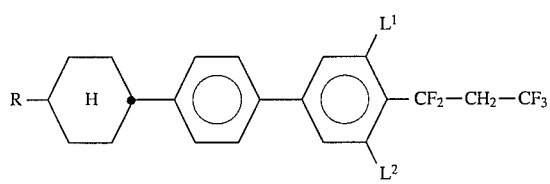

I3

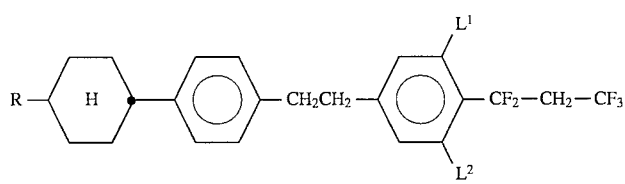

I4

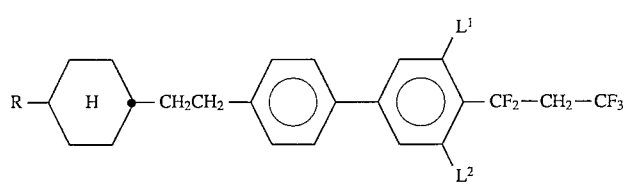

I5

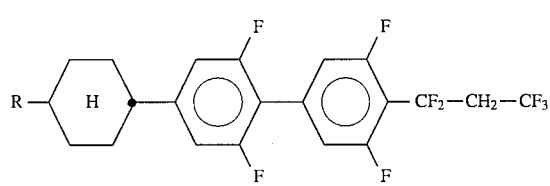

I6

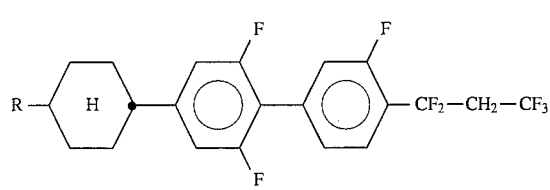

I7

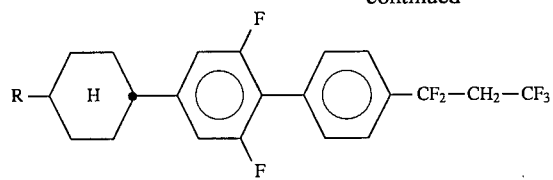
I8
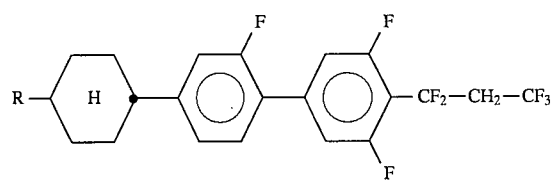
I9
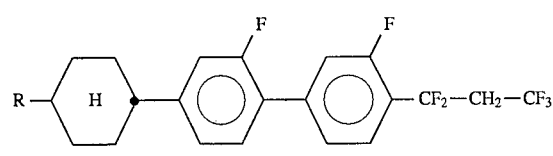
I10
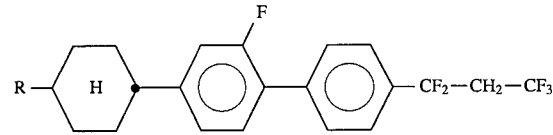
I11
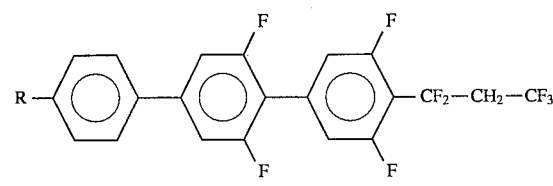
I12
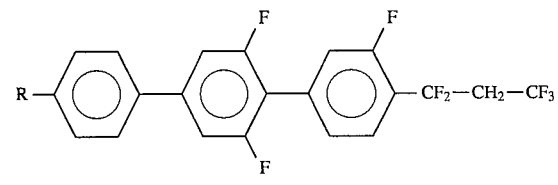
I13
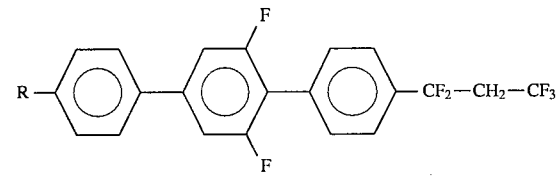
I14
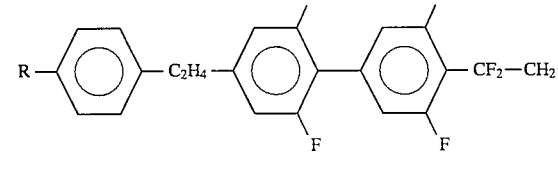
I15
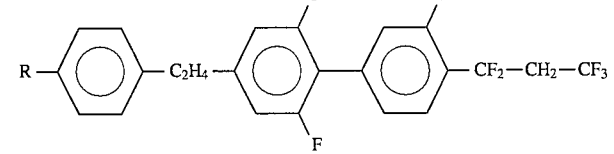
I16

-continued
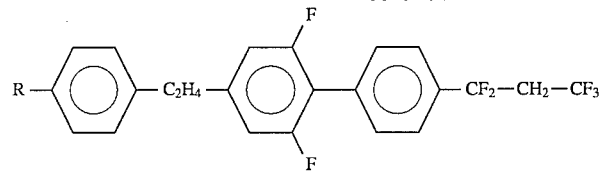 I17
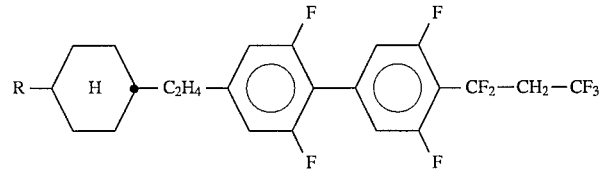 I18
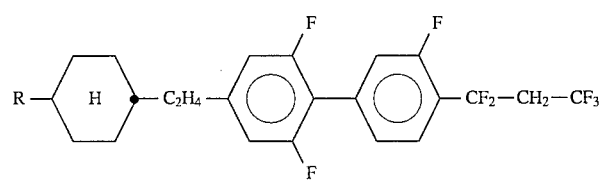 I19
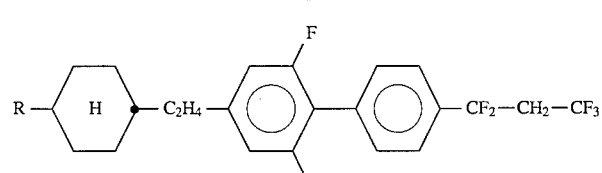 I20
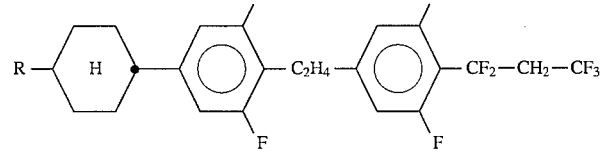 I21
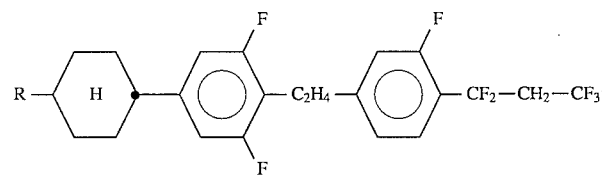 I22
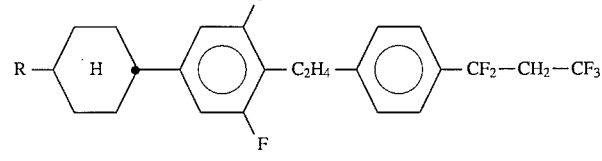 I23
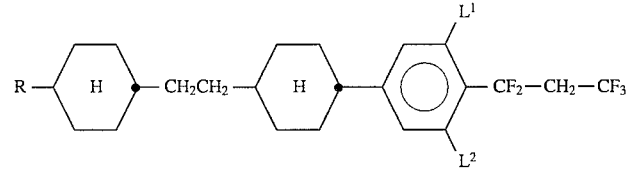 I24
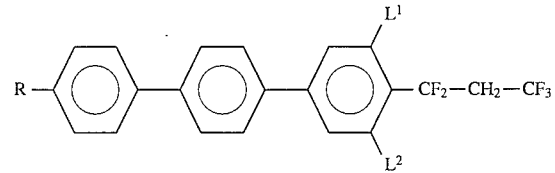 I25

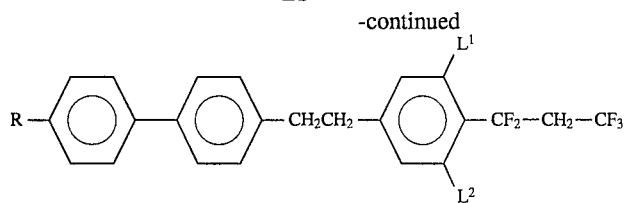

I26

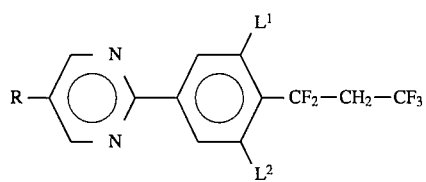

I27

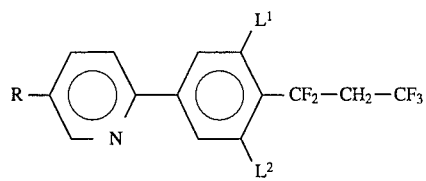

I28

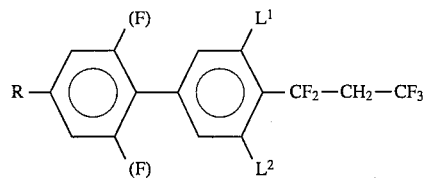

I29

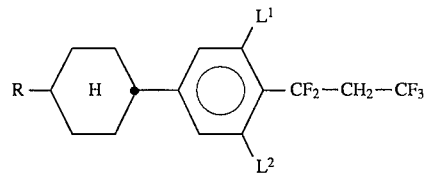

I30

Particular preference is given to compounds of the formulae I1, I3, I6, I9, I12 and I25.

The 1,4-cyclohexenylene group preferably has the following structures:

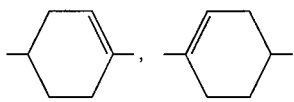

The compounds of the formula I are prepared by methods known per se, as described in the literature (for example in the standard works, such as Houben-Weyl, Methoden der Organischen Chemie (Methods of Organic Chemistry), Georg-Thieme-Verlag, Stuttgart), to be precise under reaction conditions which are known and suitable for said reactions.

Use may also be made here of variants which are known per se, but are not described here in greater detail.

The compounds of the formula I can be prepared from the corresponding ketones, obtainable by Friedel-Crafts acylation of the compounds of the formula II. The ketone is first converted into the corresponding thioketal and subsequently reacted with a brominating agent, for example 1,3-dibromo-5,5-dimethylhydantoin (NDBDH) or N-bromosuccinimide (NBS), and a fluorinating agent, such as, for example, pyridinium fluoride, tetrabutylammonium fluoride, diethylaminosulfur trifluoride (DAST) or cesium fluoride.

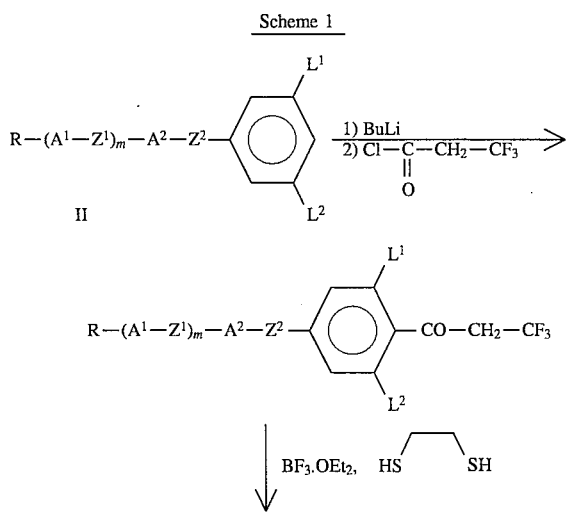

-continued
Scheme 1
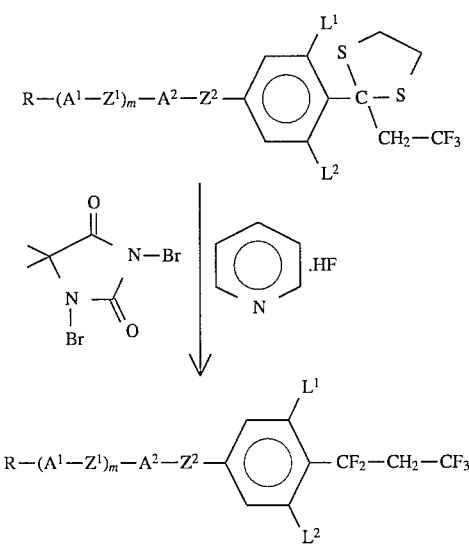
The compounds of the formula I can furthermore be prepared as follows:
Scheme 2
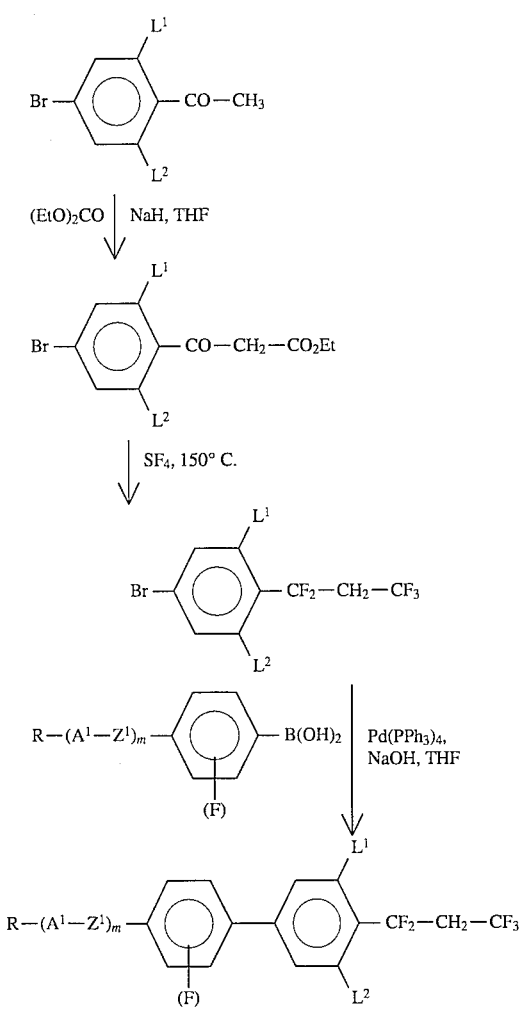
Scheme 3
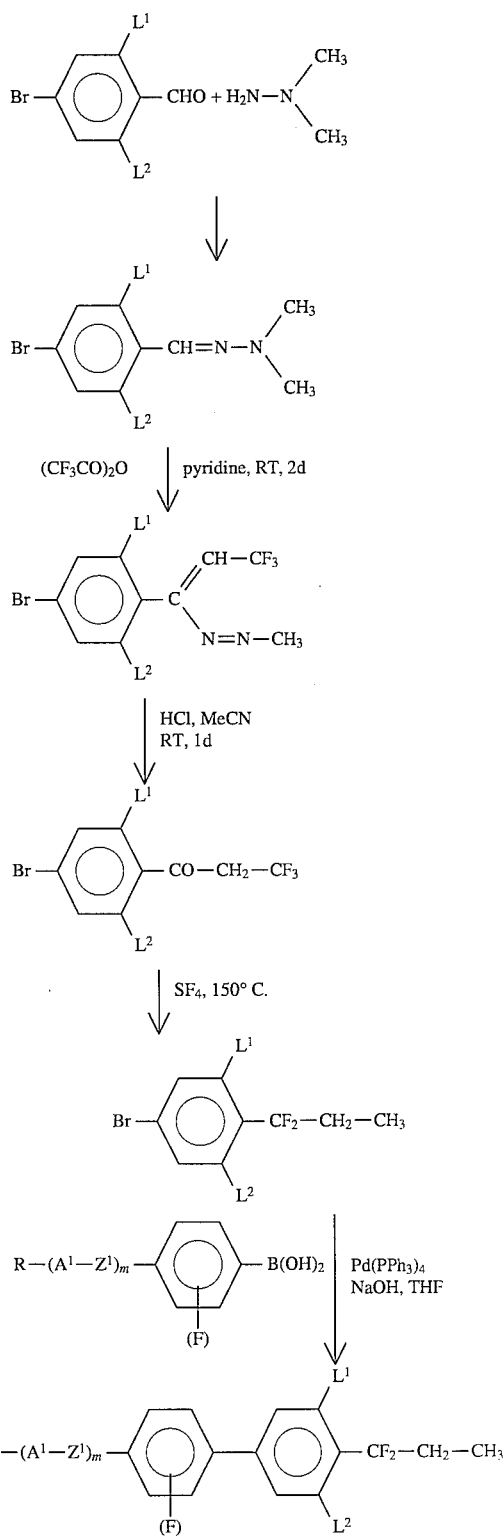
The compounds of the formula I are furthermore obtainable from the trifluoropropynebenzene derivatives, which are disclosed in EP 0 480 217.

Scheme 4
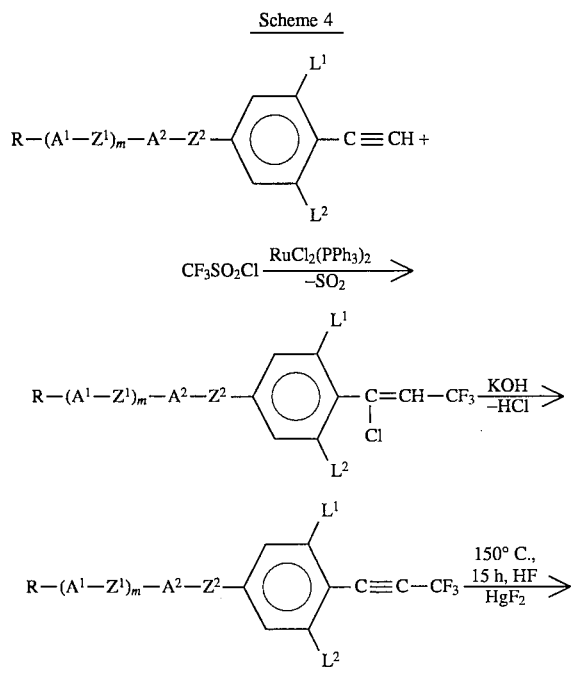
The compounds of the formula II can be prepared, for example, in accordance with the following synthesis scheme:
Scheme 5
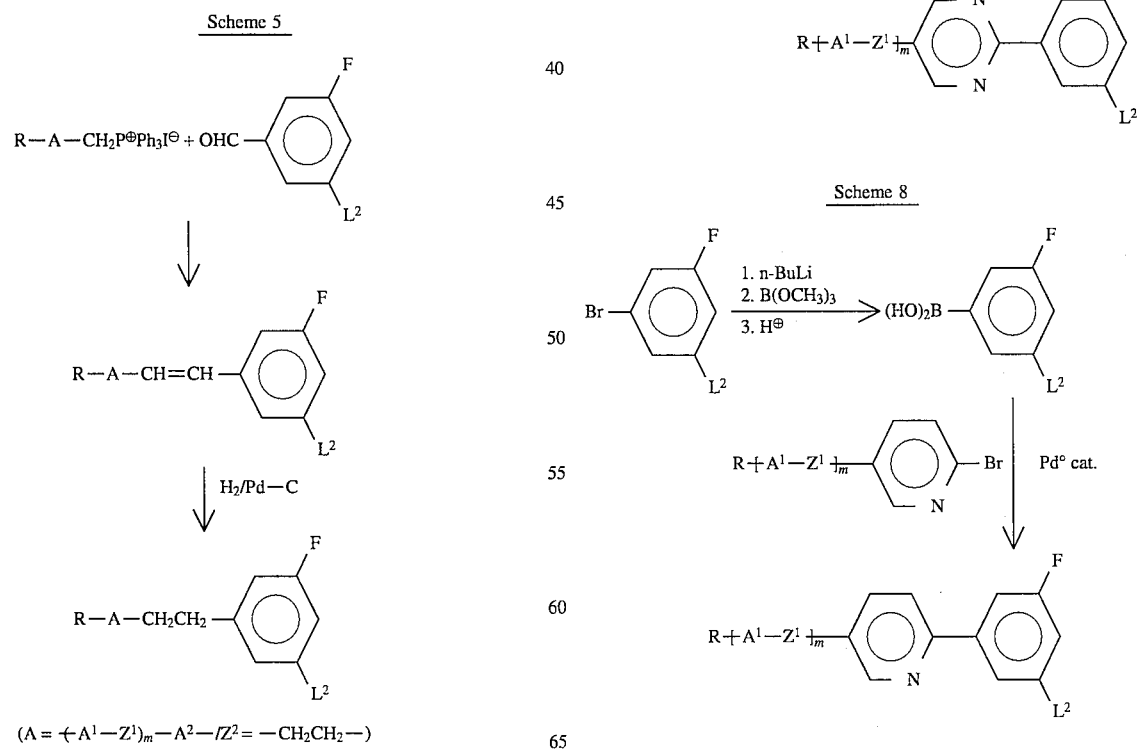
Scheme 6
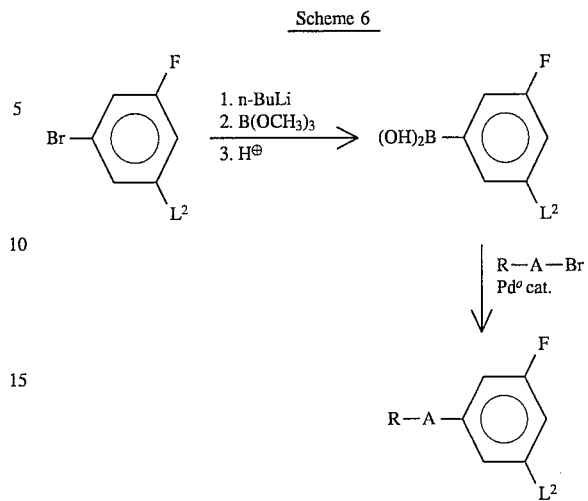
($A = -(A^1-Z^1)_m-A^2-/Z^2 =$ single bond)
Scheme 7
Scheme 8

Scheme 9

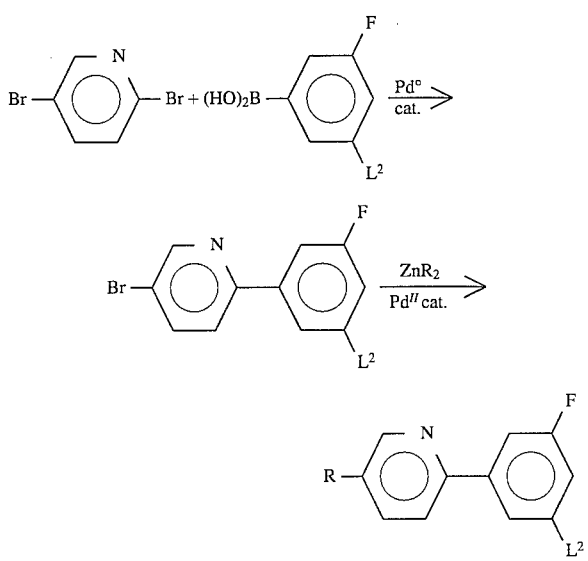

The starting materials are either known or can be prepared analogously to known compounds.

Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known methods.

In a further process for the preparation of the compounds of the formula I, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are palladium salts, in particular Pd(II) acetate, with organic phosphorus (III) compounds, such as, for example, triarylphosphines. This reaction can be carried out in the presence or absence of an inert solvent at temperatures between about 0° and 150° preferably between 20° and 100°; examples of suitable solvents are nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

In this way, it is possible to prepare, for example, stilbene derivatives. The stilbenes can furthermore be prepared by reacting a 4-substituted benzaldehyde with a corresponding phosphorus ylide by the Witrig method. However, it is also possible to prepare tolans of the formula I by employing monosubstituted acetylene in place of the olefin (Synthesis 627 (1980) or Tetrahedron Lett. 27, 1171 (1986)).

A further way of coupling aromatic compounds is to react aryl halides with aryl tin compounds. These reactions are preferably carried out with addition of a catalyst, such as, for example, a palladium(O) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I can also be prepared via the Fritsch-Buttenberg-Wiechell rearrangement (Ann. 279, 319, 1984), in which 1,1-diaryl-2-haloethylenes are rearranged in the presence of strong bases to give diaryl acetylenes.

Tolans of the formula I can also be prepared by brominating the corresponding stilbenes followed by dehydrohalogenation. Use can also be made here of variants of these reactions known per se, which are not described here in greater detail.

Ethers of the formula I can be obtained by etherification of corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide, sulfonate or dialkyl sulfate, expediently in an inert solvent, such as, for example, acetone, 1,2-dimethoxyethane, DMF or dimethyl sulfoxide, or alternatively with an excess of aqueous or aqueous-alcoholic NaOH or KOH at temperatures between about 20° and 100° C.

The starting materials are either known or can be prepared analogously to known compounds.

The compounds of the formula I' in which $Z^2=-(CH_2)_4-$ can be prepared in accordance with the following scheme:

Scheme 10

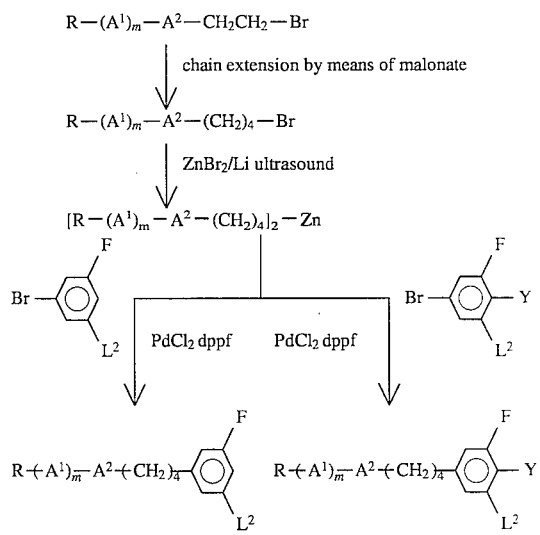

The Pd(II)-catalyzed coupling reaction either gives the target product I' directly or a precursor, into which the radical —Y is introduced entirely analogously to the above methods for compounds of the formula I.

The compounds of the formula I' in which $Z^2=-CH=CH-CH_2CH_2-$ can be prepared by the Witrig method as shown in the following scheme:

Scheme 11

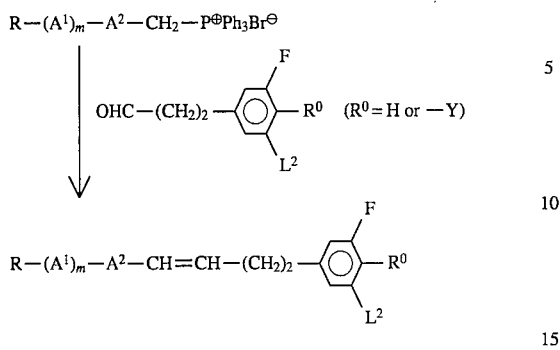

The preferred trans-isomers can be prepared by isomerization methods known from the literature. The precursors where $R^0$=H which may be obtained are converted into the compounds of the formula I' entirely analogously to the precursors of the compounds of the formula I by introduction of the radical —Y—.

The aldehydes can be obtained by Heck reaction of appropriately substituted 1-bromo-3-fluorobenzene derivatives with allyl alcohol.

The synthesis of some particularly preferred compounds is shown below in greater detail:

Scheme 12

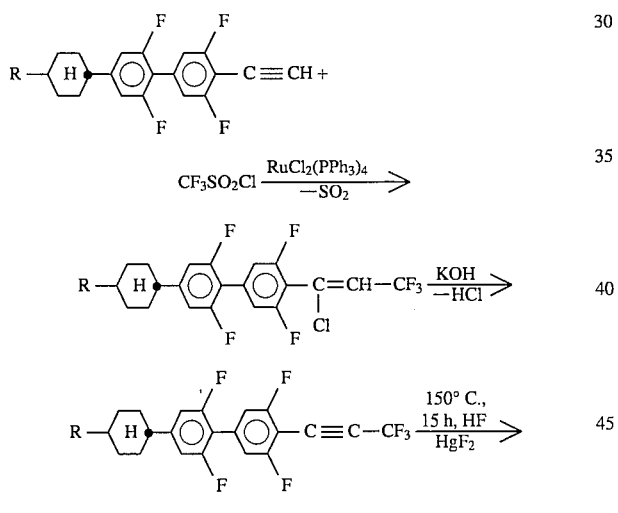

Scheme 13

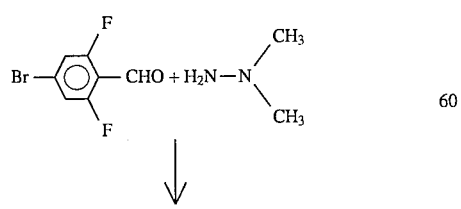

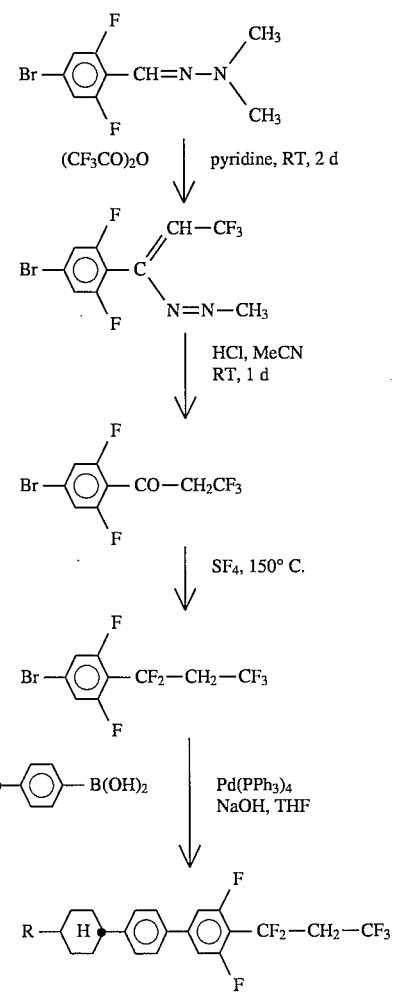

Scheme 14

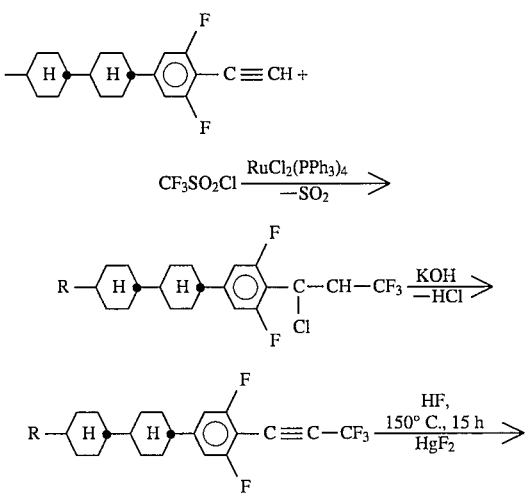

-continued
Scheme 14

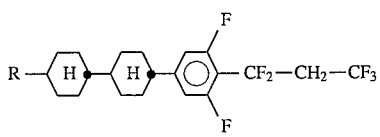

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylidene anilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenylor cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

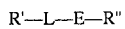    1

    2

    3

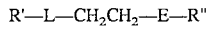    4

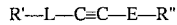    5

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group cosisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of —Phe—Phe—, —Phe— Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe— and —G—Cyc—.

In a smaller subgroup of compounds of formulae 1, 2, 3, 4 and 5 R' and R" are, in each case independently of one another, alkyl, alkenyl, alkoxy, alkoxyalkyl, alkenyloxy or alkanoyloxy having up to 8 carbon atoms. This smaller subgroup is referred to as group A below, and the compounds are labeled with the subformulae 1a, 2a, 3a, 4a and 5a. In most of these compounds, R' and R" are different from one another, one of these radicals usually being alkyl, alkenyl, alkoxy or alkoxyalkyl.

In another smaller subgroup of the compounds of the formulae 1, 2, 3, 4 and 5, known as group B, R" is —F, —Cl, —NCS or —(O)$_i$CH$_{3-(k+1)}$F$_k$Cl$_1$, where i is 0 or 1 and k+1 is 1, 2 or 3; the compounds in which R" has this meaning are labeled with the subformulae 1b, 2b, 3b, 4b and 5b. Particular preference is given to the compounds of the subformulae 1b, 2b, 3b, 4b and 5b in which R" is —F, —Cl, —NCS, —CF$_3$, —OCHF$_2$ or —OCF$_3$.

In the compounds of the subformulae 1b, 2b, 3b, 4b and 5b, R' is as defined for the compounds of the subformulae 1a–5a and is preferably alkyl, alkenyl, alkoxy or alkoxyalkyl.

In a further smaller subgroup of the compounds of the formulae 1, 2, 3, 4 and 5, R" is —CN; this subgroup is known as group C below, and the compounds of this subgroup are accordingly described by subformulae 1c, 2c, 3c, 4c and 5c. In the compounds of the subformulae 1c, 2c, 3c, 4c and 5c, R' is as defined for the compounds of the subformulae 1a–5a and is preferably alkyl, alkoxy or alkenyl.

In addition to the preferred compounds of groups A, B and C, other compounds of the formulae 1, 2, 3, 4 and 5 with other variants of the proposed substituents are also common. All these substances can be obtained by methods known from the literature or analogously thereto.

The media according to the invention preferably contain one or more compounds selected from group A and/or group B and/or group C in addition to compounds of the formula I according to the invention. The proportions by weight of the compounds from these groups in the media according to the invention are preferably Group A: from 0 to 90%, preferably 20 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50% the sum of the proportions by weight of the compounds from groups A and/or B and/or C present in the respective media according to the invention preferably being 5–90% and in particular 10–90%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the present application and in the examples below, the structures of the liquid-crystal compounds are indicated by means of acronyms, the transformation into chemical formulae being carried out in accordance with tables A and B below. All radicals $C_nH_{2n+1}$ and $C_mH_{2m+1}$ are straight-chain alkyl radicals having n or m carbon atoms respectively. The coding in table B is self-evident. In table A, only the acronym for the parent structure is shown. In individual cases, the acronym for the parent structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |

TABLE A

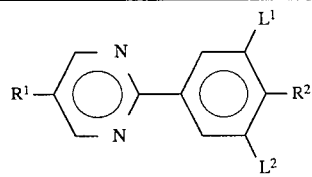

PYP

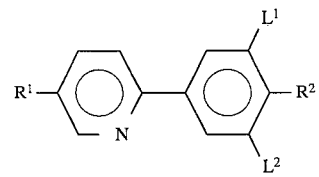

PYRP

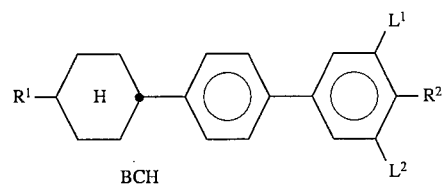

BCH

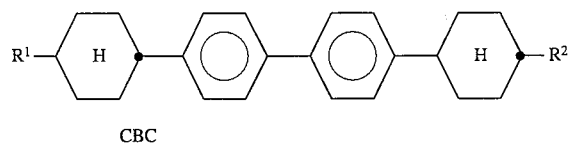

CBC

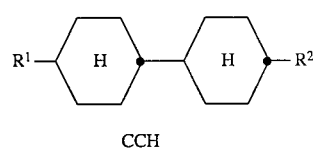

CCH

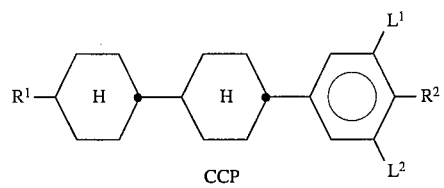

CCP

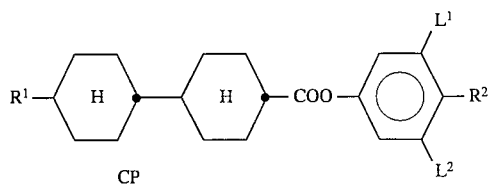

CP

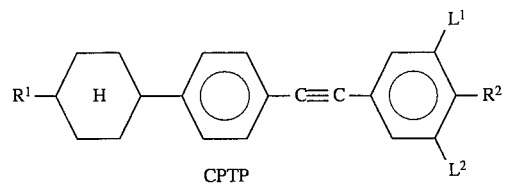

CPTP

TABLE A-continued
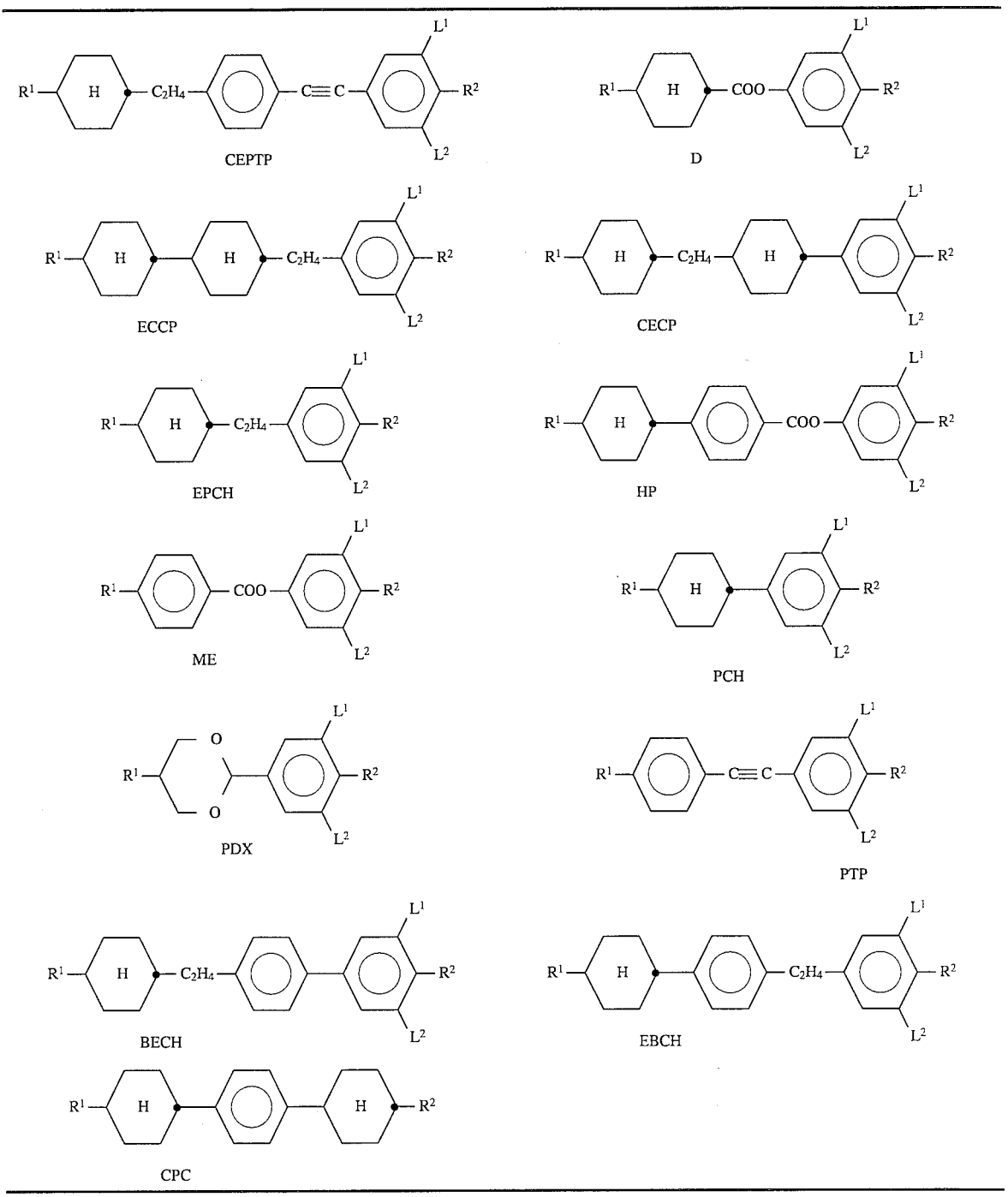
TABLE B
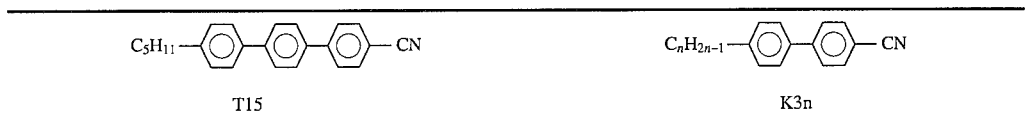

TABLE B-continued

| | |
|---|---|
| $C_nH_{2n+1}-O-\bigcirc-\bigcirc-CN$ <br> M3n | $C_nH_{2n+1}-\langle H\rangle-\bigcirc(F)-\bigcirc-C_mH_{2m+1}$ <br> BCH-n.Fm |
| $C_nH_{2n+1}-\langle H\rangle-C_2H_4-\bigcirc-\bigcirc(F)-C_mH_{2m+1}$ <br> Inm | $C_nH_{2n+1}-\langle H\rangle-\langle H\rangle-OOC-C_mH_{2m+1}$ <br> C-nm |
| $C_2H_5-\underset{*}{CH(CH_3)}-CH_2-O-\bigcirc-\bigcirc-CN$ <br> C15 | $C_2H_5-\underset{*}{CH(CH_3)}-CH_2-\bigcirc-\bigcirc-CN$ <br> CB15 |
| $C_nH_{2n+1}-\langle H\rangle-\bigcirc-\bigcirc(F)-\langle H\rangle-C_mH_{2m+1}$ <br> CBC-nmF | $C_nH_{2n+1}-\langle H\rangle-\langle H\rangle(CN,C_mH_{2m+1})$ <br> CCN-nm |
| $C_nH_{2n+1}-\langle H\rangle-\langle H\rangle-COO-\bigcirc-\langle H\rangle-C_mH_{2m+1}$ <br> CCPC-nm | |
| $C_nH_{2n+1}-\langle H\rangle-\langle H\rangle-COO-\langle H\rangle-C_mH_{2m+1}$ <br> CH-nm | $C_nH_{2n+1}-\langle H\rangle-\bigcirc-OOC-\langle H\rangle-C_mH_{2m+1}$ <br> HD-nm |
| $C_nH_{2n+1}-\langle H\rangle-\bigcirc-COO-\langle H\rangle-C_nH_{2n+1}$ <br> HH-nm | $C_nH_{2n+1}-\bigcirc-\bigcirc-\langle H\rangle(CN,C_mH_{2m+1})$ <br> NCB-nm |
| $C_nH_{2n+1}-\langle H\rangle-COO-\langle H\rangle-C_mH_{2m+1}$ <br> OS-nm | $C_2H_5-\langle H\rangle-COO-\bigcirc-\bigcirc-CN$ <br> CHE |
| $C_nH_{2n+1}-\langle H\rangle-C_2H_4-\bigcirc-\bigcirc-\langle H\rangle-C_mH_{2m+1}$ <br> ECBC-nm | |
| $C_nH_{2n+1}-\langle H\rangle-C_2H_4-\langle H\rangle-C_mH_{2m+1}$ <br> ECCH-nm | $C_nH_{2n+1}-\langle H\rangle-\langle H\rangle-CH_2O-C_mH_{2m+1}$ <br> CCH-n1EM |
| $C_nH_{2n+1}-\bigcirc(F)-\bigcirc-\bigcirc-CN$ <br> T-nFn | $C_nH_{2n+1}-\langle H\rangle-C_2H_4-\langle H\rangle-C_mH_{2m+1}$ <br> ECCH-nm |
| $C_nH_{2n+1}-\langle H\rangle-\langle H\rangle-CH_2OC_mH_{2m+1}$ <br> CCH-n1Em | $C_nH_{2n+1}-\bigcirc-\bigcirc(F)-\bigcirc-CN$ <br> T-nFN |
| $C_nH_{2n+1}-\langle H\rangle-\langle H\rangle-\bigcirc(F,F,F)$ <br> CCP-nF.F.F | $C_nH_{2n+1}-\langle H\rangle-\bigcirc(F,F)-\bigcirc(F,F)-CF_2-CH_2-CF_3$ <br> CUU-n-D1T |

TABLE B-continued

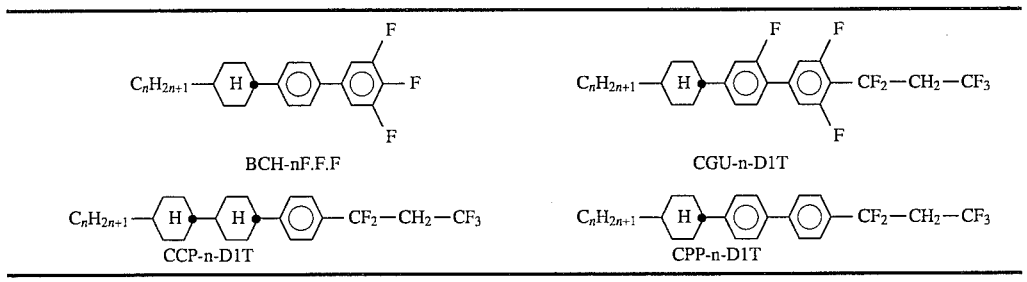

BCH-nF.F.F            CGU-n-D1T

CCP-n-D1T            CPP-n-D1T

The examples below are intended to illustrate the invention without representing a limitation. Above and below, percentages are by weight. All temperatures are given in degrees celcius. m.p. denotes melting point, c.p.=clearing point. Furthermore, C=crystalline state, N=nematic phase, S=smectic phase, I=isotropic phase. The numbers between these symbols indicate the transition temperatures. Δn denotes optical anisotropy (589 nm, 20° C.) and the viscosity (mm²/sec) was determined at 20° C.

"Conventional work-up" means that water is added if desired, the mixture is extracted with dichloromethane, diethyl ether or toluene, the organic phase is separated, dried and evaporated, and the product is purified by distillation under reduced pressure or crystallization and/or chromatography. The following abbreviations are used:

| | |
|---|---|
| DAST | Diethylaminosulfur trifluoride |
| DMEU | 1,3-Dimethyl-2-imidazoladinone |
| POT | Potassium tert-butoxide |
| THP | Tetrahydrofuran |
| pTSOH | P-Toluenesulfonic acid |

EXAMPLE 1

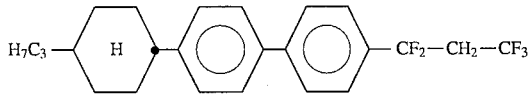

STEP 1.1

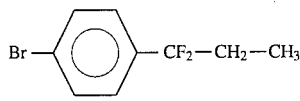

11.5 g of ethyl para-bromophenylmalonate, dissolved in 20 ml of dichloromethane, are weighed into a nickel Monell autoclave and cooled to −70° C., and 18 g of anhydrous hydrofluoric acid are added. After thawing at room temperature, the mixture is stirred for 2 hours and then cooled to −196° C., and 20 g of sulfur tetrafluoride are condensed in. The autoclave is warmed to 60° C. and left at this temperature for 2 hours. After the mixture has been cooled to room temperature, the volatile constituents are removed by distillation, the autoclave is opened, and the contents are taken up in dichloromethane. After neutralization by means of bicarbonate solution and drying over magnesium sulfate, the mixture is evaporated and distilled in vacuo.

STEP 1.2

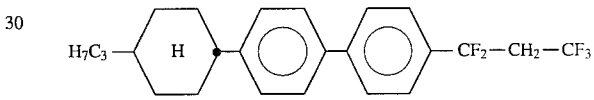

6.2 mmol of p-trans-[4-propylcyclohexyl]phenylboronic acid and 75 ml of toluene are added to 0.025 mol of NaOH and 7.5 ml of H$_2$O. The mixture is stirred at 40° C. for 15 minutes, and 6.2 mmol of p-bromo-1,1,3,3,3-pentafluoropropylbenzene and 0.14 g of tetrakistriphenylphosphinepalladium(0) are added. The mixture is subsequently heated to 100° C., refluxed for 16 hours and then allowed to cool to room temperature, and the organic phase is separated off, mixed with water and subjected to customary work-up.

The following compounds of the formula

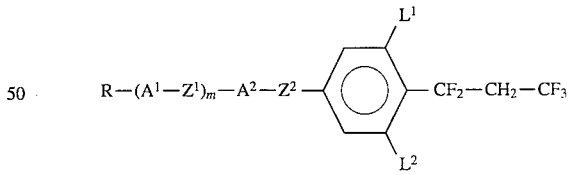

are prepared analogously:

| R | $-(A^1-Z^1)_m-A^2-Z^2-$ | $L^1$ | $L^2$ |
|---|---|---|---|
| $C_2H_5$ |  | H | H |

-continued
| R | $-(A^1-Z^1)_m-A^2-Z^2-$ | $L^1$ | $L^2$ |
|---|---|---|---|
| $C_2H_5$ | 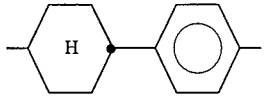 | H | F |
| $C_2H_5$ | 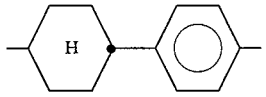 | F | F |
| n-$C_3H_7$ | 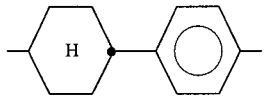 | H | F |
| n-$C_3H_7$ | 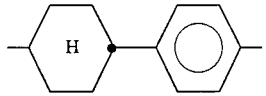 | F | F |
| n-$C_5H_{11}$ | 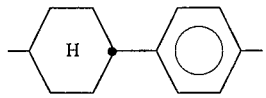 | H | H C 86 $S_B$ 113 I<br>$\Delta n = +0.133$;<br>$\Delta \epsilon = 10.67$ |
| n-$C_5H_{11}$ | 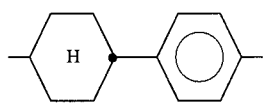 | H | F |
| n-$C_5H_{11}$ | 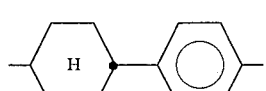 | F | F |
| n-$C_6H_{13}$ | 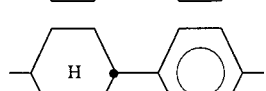 | H | H |
| n-$C_6H_{13}$ | 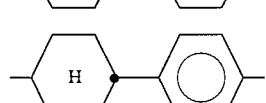 | H | F |
| n-$C_6H_{13}$ | 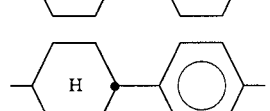 | F | F |
| $CH_2=CHCH_2$ |  | H | H |
| $CH_2=CHCH_2$ | 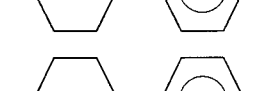 | H | F |
| $CH_2=CHCH_2$ |  | F | F |
| n-$C_3H_7$ |  | H | H |
| n-$C_3H_7$ | 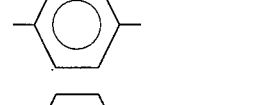 | H | F |

-continued
| R | $-(A^1-Z^1)_m-A^2-Z^2-$ | $L^1$ | $L^2$ |
|---|---|---|---|
| n-C$_3$H$_7$ |  | F | F |
| n-C$_5$H$_{11}$ | 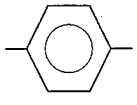 | F | F |
| n-C$_5$H$_{11}$ | 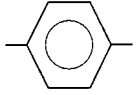 | H | H |
| n-C$_5$H$_{11}$ | 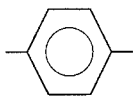 | H | F |
| CH$_3$O |  | F | F |
| CH$_3$O | 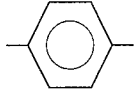 | H | H |
| CH$_3$O |  | H | F |
| CH$_2$=CHCH$_2$ |  | H | H |
| CH$_2$=CHCH$_2$ | 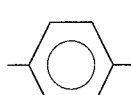 | H | F |
| CH$_2$=CHCH$_2$ | 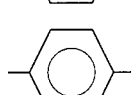 | F | F |
| C$_2$H$_5$ | 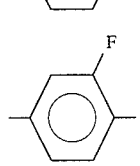 | H | H |
| C$_2$H$_5$ | 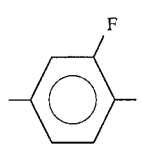 | H | F |
| C$_2$H$_5$ | 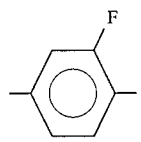 | F | F |

-continued
| R | $-(A^1-Z^1)_m-A^2-Z^2-$ | $L^1$ | $L^2$ |
|---|---|---|---|
| n-$C_3H_7$ | 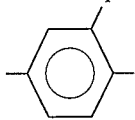 | H | H |
| n-$C_3H_7$ | 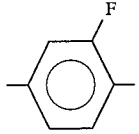 | H | F |
| n-$C_3H_7$ | 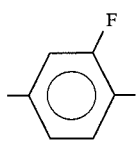 | F | F |
| n-$C_5H_{11}$ | 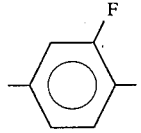 | F | F |
| n-$C_5H_{11}$ | 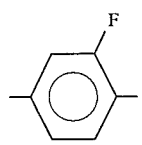 | H | H |
| n-$C_5H_{11}$ | 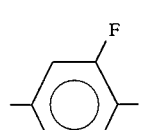 | H | F |
| $CH_3O$ | 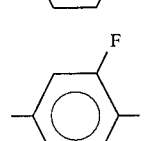 | F | F |
| $CH_3O$ | 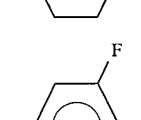 | H | H |
| $CH_3O$ | 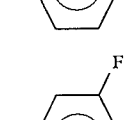 | H | F |
| $CH_2=CHCH_2$ | 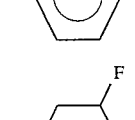 | H | H |
| $CH_2=CHCH_2$ | 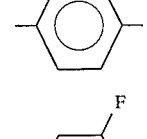 | H | F |

-continued
| R | $-(A^1-Z^1)_m-A^2-Z^2-$ | $L^1$ | $L^2$ |
|---|---|---|---|
| $CH_2=CHCH_2$ | 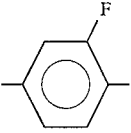 | F | F |
| $C_2H_5$ | 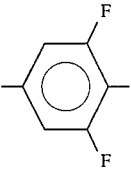 | H | H |
| $C_2H_5$ | 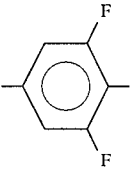 | H | F |
| $C_2H_5$ | 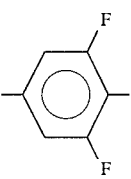 | F | F |
| $n\text{-}C_3H_7$ | 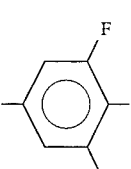 | H | H |
| $n\text{-}C_3H_7$ | 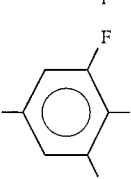 | H | F |
| $n\text{-}C_3H_7$ | 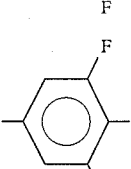 | F | F |
| $n\text{-}C_5H_{11}$ | 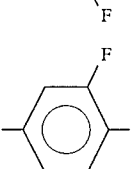 | F | F |
| $n\text{-}C_5H_{11}$ | 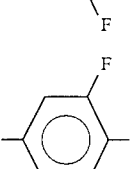 | H | H |

-continued
| R | $-(A^1-Z^1)_m-A^2-Z^2-$ | $L^1$ | $L^2$ |
|---|---|---|---|
| n-C$_5$H$_{11}$ | 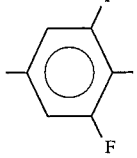 | H | F |
| C$_2$H$_5$ | 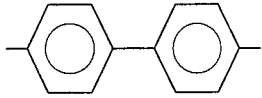 | H | H |
| C$_2$H$_5$ | 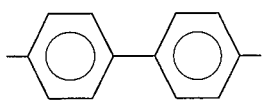 | H | F |
| C$_2$H$_5$ | 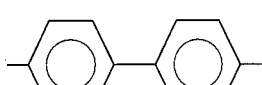 | F | F |
| n-C$_3$H$_7$ | 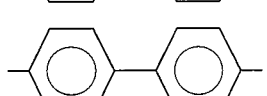 | H | H |
| n-C$_3$H$_7$ | 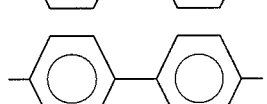 | H | F |
| n-C$_3$H$_7$ |  | F | F |
| n-C$_5$H$_{11}$ |  | F | F |
| n-C$_5$H$_{11}$ |  | H | H |
| n-C$_5$H$_{11}$ |  | H | F |
| CH$_3$O |  | F | F |
| CH$_3$O | 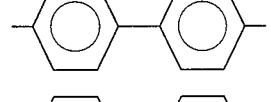 | H | H |
| CH$_3$O | 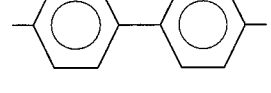 | H | F |
| CH$_2$=CHCH$_2$ | 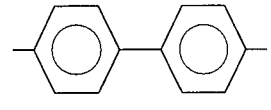 | H | H |

-continued
| R | $-(A^1-Z^1)_m-A^2-Z^2-$ | $L^1$ | $L^2$ |
|---|---|---|---|
| $CH_2=CHCH_2$ | 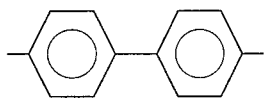 | H | F |
| $CH_2=CHCH_2$ | 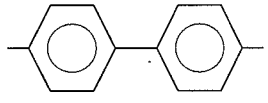 | F | F |
| $C_2H_5$ | 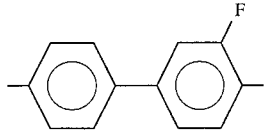 | H | H |
| $C_2H_5$ | 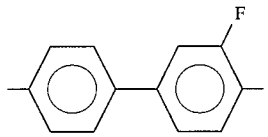 | H | F |
| $C_2H_5$ | 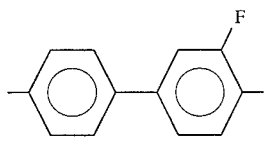 | F | F |
| $n-C_3H_7$ | 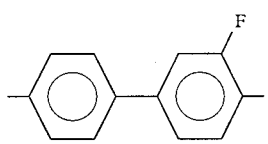 | H | H |
| $n-C_3H_7$ | 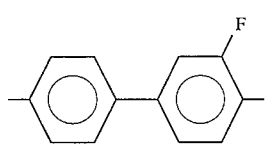 | H | F |
| $n-C_3H_7$ | 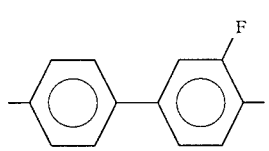 | F | F |
| $n-C_5H_{11}$ | 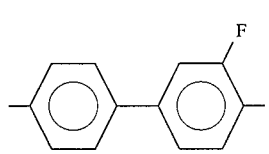 | F | F |
| $n-C_5H_{11}$ | 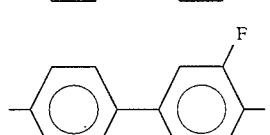 | H | H |
| $n-C_5H_{11}$ | 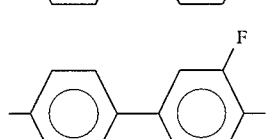 | H | F |

-continued
| R | $-(A^1-Z^1)_m-A^2-Z^2-$ | $L^1$ | $L^2$ |
|---|---|---|---|
| CH$_3$O | 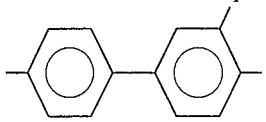 | F | F |
| CH$_3$O | 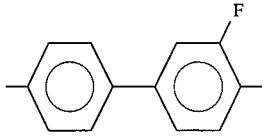 | H | H |
| CH$_3$O | 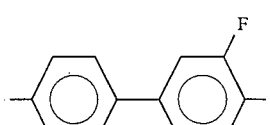 | H | F |
| CH$_2$=CHCH$_2$ | 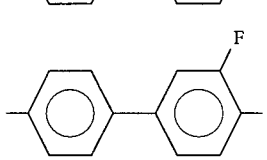 | H | H |
| CH$_2$=CHCH$_2$ | 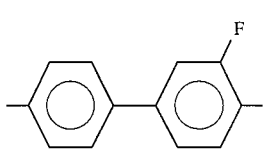 | H | F |
| CH$_2$=CHCH$_2$ | 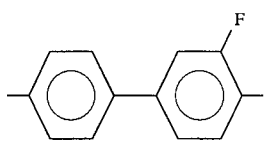 | F | F |
| C$_2$H$_5$ | 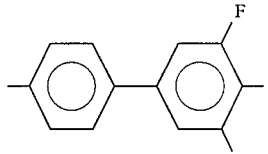 | H | H |
| C$_2$H$_5$ | 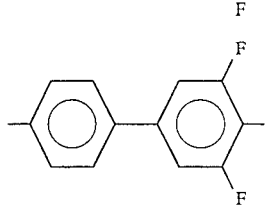 | H | F |
| C$_2$H$_5$ | 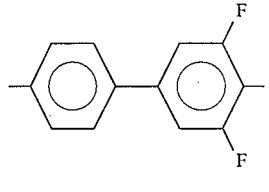 | F | F |
| n-C$_3$H$_7$ | 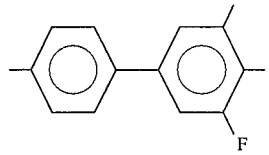 | H | H |

| R | $-(A^1-Z^1)_m-A^2-Z^2-$ | $L^1$ | $L^2$ |
|---|---|---|---|
| n-C$_3$H$_7$ | 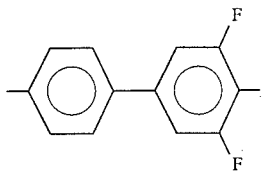 | H | F |
| n-C$_3$H$_7$ | 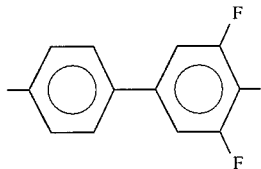 | F | F |
| n-C$_5$H$_{11}$ | 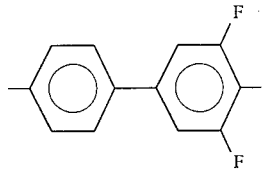 | F | F |
| n-C$_5$H$_{11}$ | 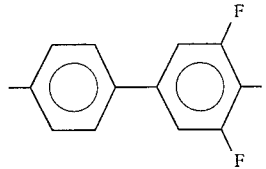 | H | H |
| n-C$_5$H$_{11}$ | 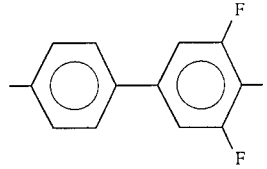 | H | F |
| n-C$_3$H$_7$ | 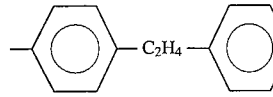 | H | H |
| n-C$_3$H$_7$ | 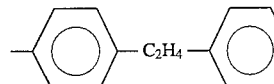 | H | F |
| n-C$_3$H$_7$ | 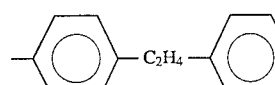 | F | F |
| n-C$_5$H$_{11}$ | 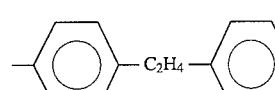 | F | F |
| n-C$_5$H$_{11}$ | 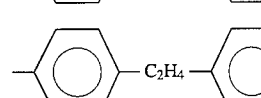 | H | H |
| n-C$_5$H$_{11}$ | 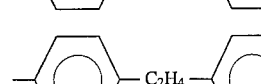 | H | F |

-continued
| R | $-(A^1-Z^1)_m-A^2-Z^2-$ | $L^1$ | $L^2$ |
|---|---|---|---|
| n-C$_3$H$_7$ | 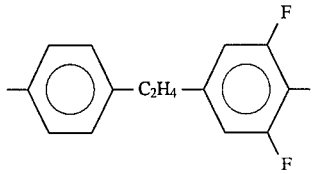 | H | H |
| n-C$_3$H$_7$ | 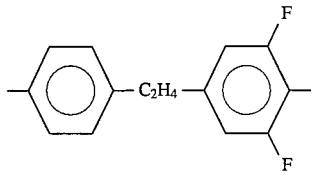 | H | F |
| n-C$_3$H$_7$ | 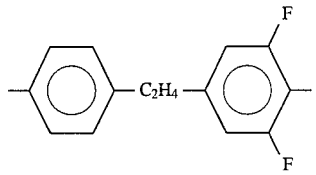 | F | F |
| n-C$_5$H$_{11}$ | 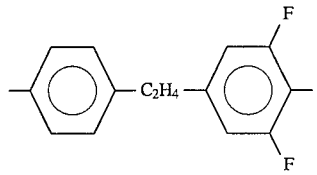 | F | F |
| n-C$_5$H$_{11}$ | 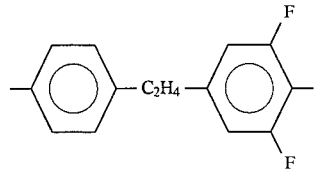 | H | H |
| n-C$_5$H$_{11}$ | 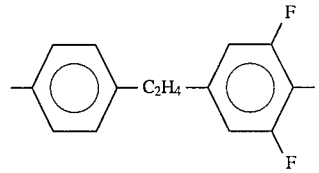 | H | F |
| CH$_3$O | 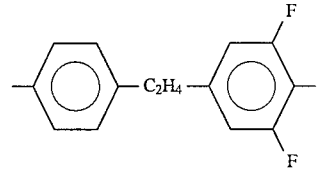 | F | F |
| CH$_3$O | 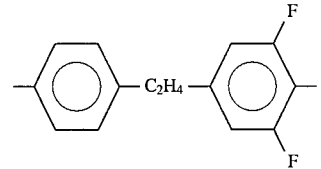 | H | H |
| CH$_3$O | 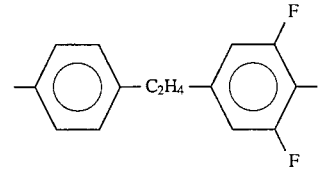 | H | F |

-continued
| R | $-(A^1-Z^1)_m-A^2-Z^2-$ | $L^1$ | $L^2$ |
|---|---|---|---|
| $CH_2=CHCH_2$ | 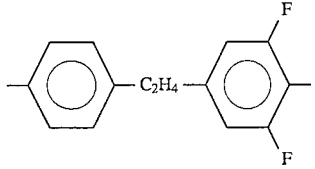 | H | H |
| $CH_2=CHCH_2$ | 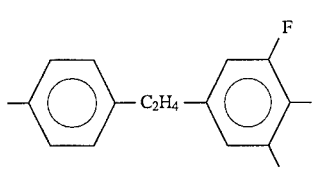 | H | F |
| $CH_2=CHCH_2$ | 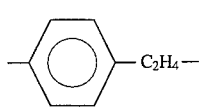 | F | F |
| $C_2H_5$ | 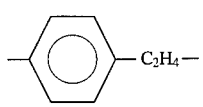 | H | H |
| $C_2H_5$ | 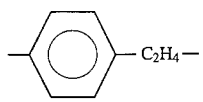 | H | F |
| $C_2H_5$ | 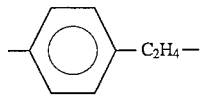 | F | F |
| n-$C_3H_7$ | 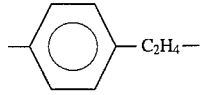 | H | H |
| n-$C_3H_7$ | 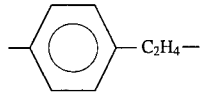 | H | F |
| n-$C_3H_7$ | 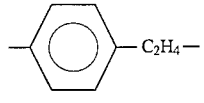 | F | F |
| n-$C_5H_{11}$ | 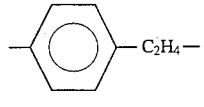 | F | F |
| n-$C_5H_{11}$ | 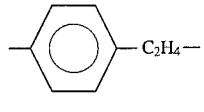 | H | H |
| n-$C_5H_{11}$ | | H | F |

-continued

| R | −(A¹−Z¹)ₘ−A²−Z²− | L¹ | L² |
|---|---|---|---|
| CH₃O | —⬡—C₂H₄— | F | F |
| CH₃O | —⬡—C₂H₄— | H | H |
| CH₃O | —⬡—C₂H₄— | H | F |
| CH₂=CHCH₂ | —⬡—C₂H₄— | H | H |
| CH₂=CHCH₂ | —⬡—C₂H₄— | H | F |
| CH₂=CHCH₂ | —⬡—C₂H₄— | F | F |
| C₂H₅ | —⬡—⬡—C₂H₄— | H | H |
| C₂H₅ | —⬡—⬡—C₂H₄— | H | F |
| C₂H₅ | —⬡—⬡—C₂H₄— | F | F |
| n-C₃H₇ | —⬡—⬡—C₂H₄— | H | H |
| n-C₃H₇ | —⬡—⬡—C₂H₄— | H | F |
| n-C₃H₇ | —⬡—⬡—C₂H₄— | F | F |
| n-C₅H₁₁ | —⬡—⬡—C₂H₄— | F | F |
| n-C₅H₁₁ | —⬡—⬡—C₂H₄— | H | H |
| n-C₅H₁₁ | —⬡—⬡—C₂H₄— | H | F |

-continued
| R | $-(A^1-Z^1)_m-A^2-Z^2-$ | $L^1$ | $L^2$ |
|---|---|---|---|
| CH$_3$O | 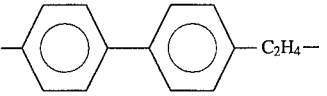 | F | F |
| CH$_3$O | 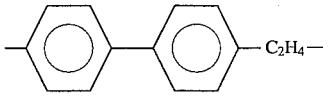 | H | H |
| CH$_3$O | 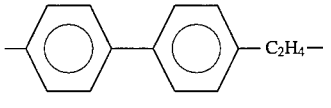 | H | F |
| CH$_2$=CHCH$_2$ | 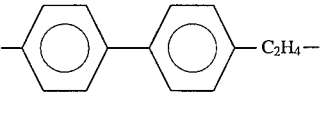 | H | H |
| CH$_2$=CHCH$_2$ |  | H | F |
| CH$_2$=CHCH$_2$ | 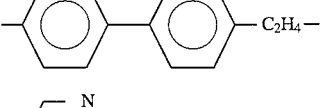 | F | F |
| n-C$_3$H$_7$ | 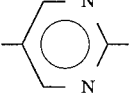 | H | H |
| n-C$_3$H$_7$ | 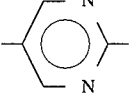 | H | F |
| n-C$_3$H$_7$ | 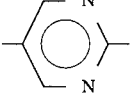 | F | F |
| n-C$_5$H$_{11}$ | 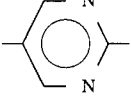 | F | F |
| n-C$_5$H$_{11}$ | 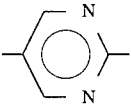 | H | H |
| n-C$_5$H$_{11}$ | 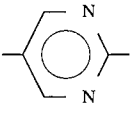 | H | F |
| n-C$_3$H$_7$ | 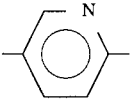 | H | H |
| n-C$_3$H$_7$ | 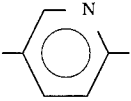 | H | F |

| R | $-(A^1-Z^1)_m-A^2-Z^2-$ | $L^1$ | $L^2$ |
|---|---|---|---|
| n-C₃H₇ | 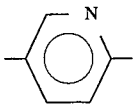 | F | F |
| n-C₅H₁₁ | 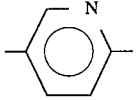 | F | F |
| n-C₅H₁₁ | 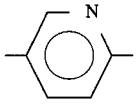 | H | H |
| n-C₅H₁₁ | 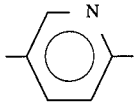 | H | F |

EXAMPLE 2

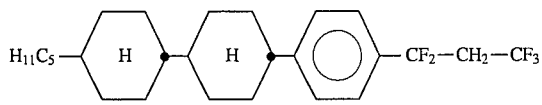

0.1 mol of trans-4-(trans-4-pentylcyclohexyl)cyclohexyl bromide, 0.05 mol of zinc bromide and 0.2 mol of lithium granules in 150 ml of toluene/THF (4:1) are treated with ultrasound at 15° C. for 3 hours under a nitrogen atmosphere. p-Bromo-1,1,3,3,3-pentafluoropropylbenzene and 1.2 g of bis(diphenylphosphine)ferrocenepalladium(II) chloride are added, and the mixture is stirred at room temperature for 72 hours.

100 ml of saturated ammonium chloride solution are added dropwise to the solution, and the mixture is subsequently stirred for 15 minutes. The organic phase is separated off and subjected to customary work-up. C 55 $S_M$ (52) $S_G$ 127 $S_B$ 128 I The following compounds of the formula

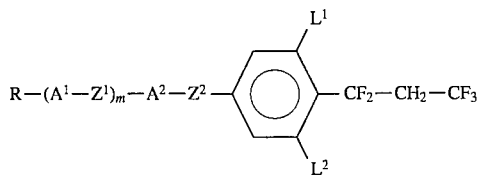

are prepared analogously:

| R | $-(A^1-Z^1)_m-A^2-Z^2-$ | $L^1$ | $L^2$ |
|---|---|---|---|
| C₂H₅ | 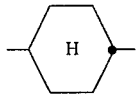 | H | H |
| C₂H₅ | 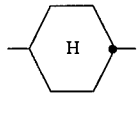 | H | F |
| C₂H₅ | 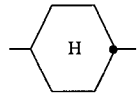 | F | F |
| n-C₃H₇ | 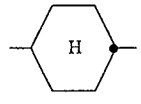 | H | H |
| n-C₃H₇ | 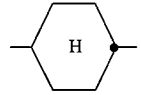 | H | F |
| n-C₃H₇ | 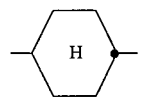 | F | F |
| n-C₅H₁₁ | 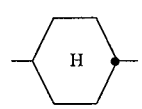 | H | H |
| n-C₅H₁₁ | 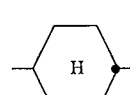 | H | F |
| n-C₅H₁₁ | 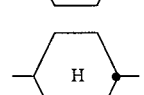 | F | F |
| n-C₆H₁₃ | 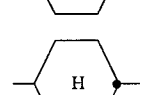 | H | H |
| n-C₆H₁₃ | 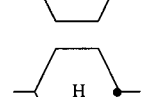 | H | F |

| R | $-(A^1-Z^1)_m-A^2-Z^2-$ | $L^1$ | $L^2$ |
|---|---|---|---|
| n-C$_6$H$_{13}$ | 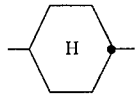 | F | F |
| CH$_2$=CHCH$_2$ | 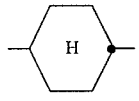 | H | H |
| CH$_2$=CHCH$_2$ | 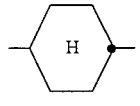 | H | F |
| CH$_2$=CHCH$_2$ | 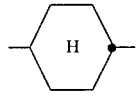 | F | F |
| C$_2$H$_5$ | 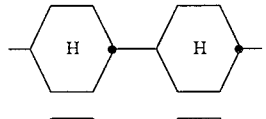 | H | H |
| C$_2$H$_5$ |  | H | F |
| C$_2$H$_5$ | 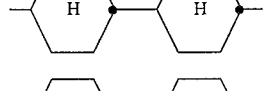 | F | F |
| n-C$_3$H$_7$ |  | H | H |
| n-C$_3$H$_7$ | 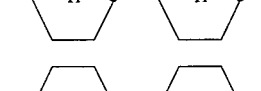 | H | F |
| n-C$_3$H$_7$ | 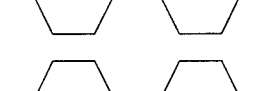 | F | F |
| n-C$_5$H$_{11}$ | 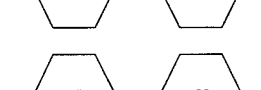 | H | F |
| n-C$_5$H$_{11}$ |  | F | F |
| n-C$_6$H$_{13}$ |  | H | H |
| n-C$_6$H$_{13}$ |  | H | F |
| n-C$_6$H$_{13}$ |  | F | F |

| R | $-(A^1-Z^1)_m-A^2-Z^2-$ | $L^1$ | $L^2$ |
|---|---|---|---|
| CH$_2$=CHCH$_2$ | 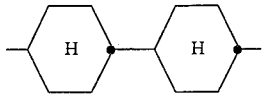 | H | H |
| CH$_2$=CHCH$_2$ | 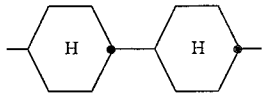 | H | F |
| CH$_2$=CHCH$_2$ | 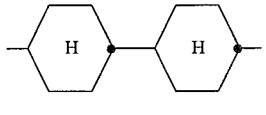 | F | F |
| C$_2$H$_5$ | 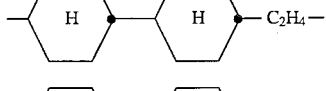 | H | H |
| C$_2$H$_5$ | 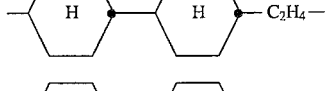 | H | F |
| C$_2$H$_5$ | 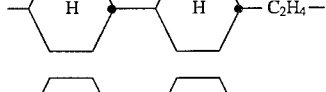 | F | F |
| n-C$_3$H$_7$ | 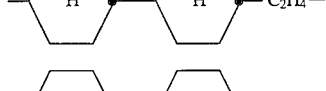 | H | H |
| n-C$_3$H$_7$ | 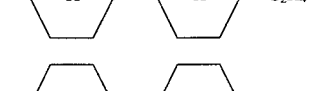 | H | F |
| n-C$_3$H$_7$ | 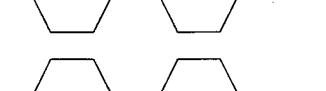 | F | F |
| n-C$_5$H$_{11}$ | 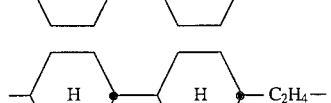 | H | H |
| n-C$_5$H$_{11}$ | 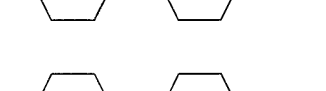 | H | F |
| n-C$_5$H$_{11}$ | 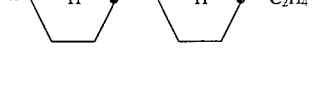 | F | F |
| n-C$_6$H$_{13}$ | 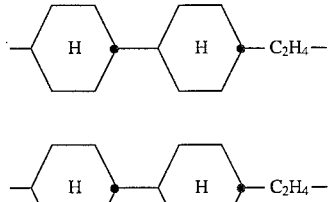 | H | H |

5,571,449

61
-continued

| R | $-(A^1-Z^1)_m-A^2-Z^2-$ | $L^1$ | $L^2$ |
|---|---|---|---|
| n-C$_6$H$_{13}$ | 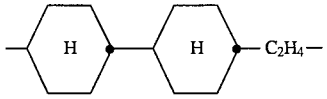 | F | F |
| CH$_2$=CHCH$_2$ | 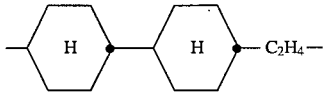 | H | H |
| CH$_2$=CHCH$_2$ | 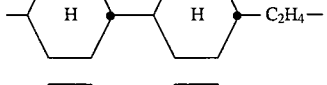 | H | F |
| CH$_2$=CHCH$_2$ |  | F | F |
| C$_2$H$_5$ |  | H | H |
| C$_2$H$_5$ | 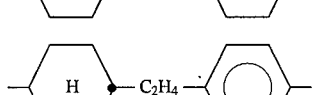 | H | F |
| C$_2$H$_5$ | 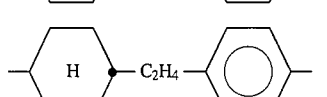 | F | F |
| n-C$_3$H$_7$ | 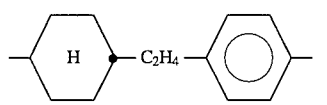 | H | H |
| n-C$_3$H$_7$ | 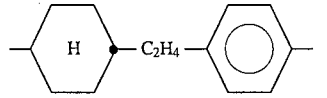 | H | F |
| n-C$_3$H$_7$ | 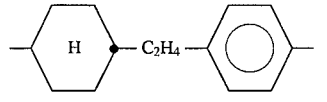 | F | F |
| n-C$_5$H$_{11}$ | 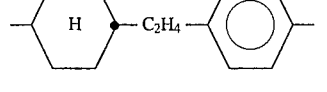 | H | H |
| n-C$_5$H$_{11}$ | 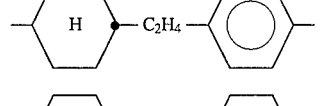 | H | F |
| n-C$_5$H$_{11}$ |  | F | F |
| n-C$_6$H$_{13}$ |  | H | H |
| n-C$_6$H$_{13}$ |  | H | F |

62
-continued

| R | $-(A^1-Z^1)_m-A^2-Z^2-$ | $L^1$ | $L^2$ |
|---|---|---|---|
| n-C$_6$H$_{13}$ | 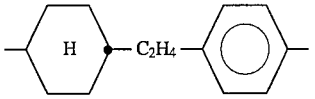 | F | F |
| CH$_2$=CHCH$_2$ | 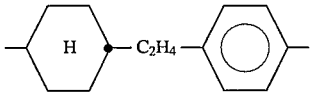 | H | H |
| CH$_2$=CHCH$_2$ | 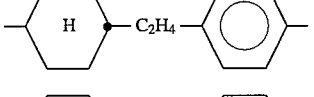 | H | F |
| CH$_2$=CHCH$_2$ | 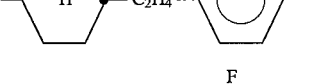 | F | F |
| C$_2$H$_5$ | 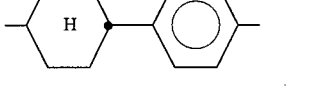 | H | H |
| C$_2$H$_5$ | 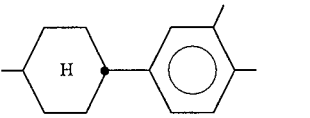 | H | F |
| C$_2$H$_5$ | 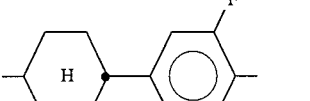 | F | F |
| n-C$_3$H$_7$ |  | H | H |
| n-C$_3$H$_7$ |  | H | F |
| n-C$_3$H$_7$ |  | F | F |
| n-C$_5$H$_{11}$ | 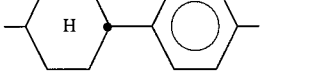 | H | H |
| n-C$_5$H$_{11}$ | 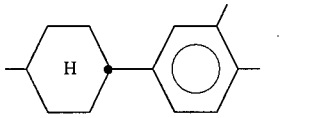 | H | F |

| R | $-(A^1-Z^1)_m-A^2-Z^2-$ | L¹ | L² |
|---|---|---|---|
| n-C₅H₁₁ | cyclohexyl-phenyl, 3-F | F | F |
| n-C₆H₁₃ | cyclohexyl-phenyl, 3-F | H | H |
| n-C₆H₁₃ | cyclohexyl-phenyl, 3-F | H | F |
| n-C₆H₁₃ | cyclohexyl-phenyl, 3-F | F | F |
| CH₂=CHCH₂ | cyclohexyl-phenyl, 3-F | H | H |
| CH₂=CHCH₂ | cyclohexyl-phenyl, 3-F | H | F |
| CH₂=CHCH₂ | cyclohexyl-phenyl, 3-F | F | F |
| C₂H₅ | cyclohexyl-phenyl, 3,5-F₂ | H | H |
| C₂H₅ | cyclohexyl-phenyl, 3,5-F₂ | H | F |
| C₂H₅ | cyclohexyl-phenyl, 3,5-F₂ | F | F |
| n-C₃H₇ | cyclohexyl-phenyl, 3-F | H | H |
| n-C₃H₇ | cyclohexyl-phenyl, 3,5-F₂ | H | F |
| n-C₃H₇ | cyclohexyl-phenyl, 3,5-F₂ | F | F |
| n-C₅H₁₁ | cyclohexyl-phenyl, 3,5-F₂ | H | H |
| n-C₅H₁₁ | cyclohexyl-phenyl, 3,5-F₂ | H | F |
| n-C₅H₁₁ | cyclohexyl-phenyl, 3,5-F₂ | F | F |
| n-C₆H₁₃ | cyclohexyl-phenyl, 3,5-F₂ | H | H |
| n-C₆H₁₃ | cyclohexyl-phenyl, 3,5-F₂ | H | F |
| n-C₆H₁₃ | cyclohexyl-phenyl, 3,5-F₂ | F | F |

| R | $-(A^1-Z^1)_m-A^2-Z^2-$ | $L^1$ | $L^2$ |
|---|---|---|---|
| CH₂=CHCH₂ | Cy–Ph(F,F) | H | H |
| CH₂=CHCH₂ | Cy–Ph(F,F) | H | F |
| CH₂=CHCH₂ | Cy–Ph(F,F) | F | F |
| n-C₃H₇ | Cy–C₂H₄–Ph(F,F) | H | H |
| n-C₃H₇ | Cy–C₂H₄–Ph(F,F) | H | F |
| n-C₃H₇ | Cy–C₂H₄–Ph(F,F) | F | F |
| n-C₅H₁₁ | Cy–C₂H₄–Ph(F,F) | H | H |
| n-C₅H₁₁ | Cy–C₂H₄–Ph(F,F) | H | F |
| n-C₅H₁₁ | Cy–C₂H₄–Ph(F,F) | F | F |
| n-C₆H₁₃ | Cy–C₂H₄–Ph(F,F) | H | H |
| n-C₆H₁₃ | Cy–C₂H₄–Ph(F,F) | H | F |
| n-C₆H₁₃ | Cy–C₂H₄–Ph(F,F) | F | F |
| CH₂=CHCH₂ | Cy–C₂H₄–Ph(F,F) | H | H |
| CH₂=CHCH₂ | Cy–C₂H₄–Ph(F,F) | H | F |
| CH₂=CHCH₂ | Cy–C₂H₄–Ph(F,F) | F | F |
| C₂H₅ | Cy–C₂H₄–Cy | H | H |
| C₂H₅ | Cy–C₂H₄–Cy | H | F |
| C₂H₅ | Cy–C₂H₄–Cy | F | F |
| n-C₃H₇ | Cy–C₂H₄–Cy | H | H |

| R | $-(A^1-Z^1)_m-A^2-Z^2-$ | $L^1$ | $L^2$ |
|---|---|---|---|
| n-C₃H₇ | 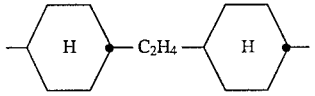 | H | F |
| n-C₃H₇ | 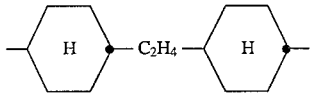 | F | F |
| n-C₅H₁₁ | 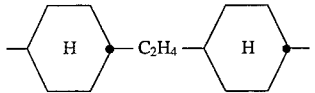 | H | H |
| n-C₅H₁₁ | 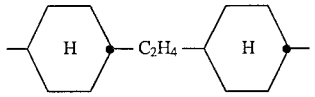 | H | F |
| n-C₅H₁₁ | 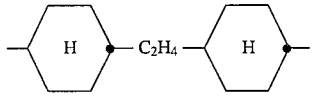 | F | F |
| n-C₆H₁₃ | 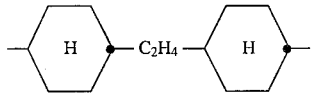 | H | H |
| n-C₆H₁₃ | 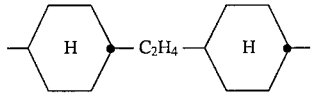 | H | F |
| n-C₆H₁₃ | 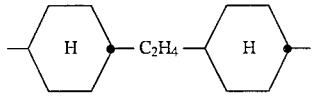 | F | F |
| CH₂=CHCH₂ | 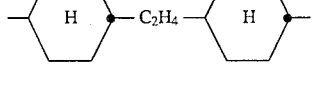 | H | H |
| CH₂=CHCH₂ | 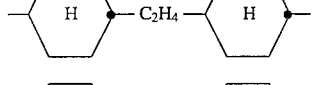 | H | F |
| CH₂=CHCH₂ | 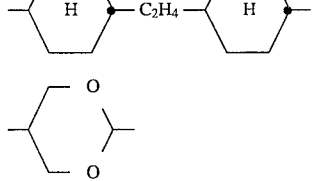 | F | F |
| n-C₃H₇ |  | H | H |
| n-C₃H₇ |  | H | F |
| n-C₃H₇ |  | F | F |

| R | $-(A^1-Z^1)_m-A^2-Z^2-$ | $L^1$ | $L^2$ |
|---|---|---|---|
| n-C₅H₁₁ | 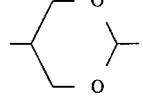 | H | H |
| n-C₅H₁₁ | 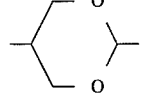 | H | F |
| n-C₅H₁₁ | 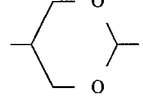 | F | F |
| n-C₃H₇ | 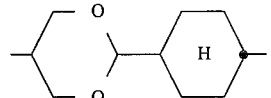 | H | H |
| n-C₃H₇ | 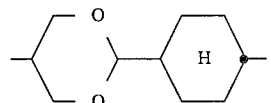 | H | F |
| n-C₃H₇ | 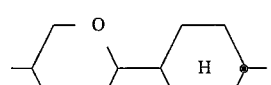 | F | F |
| n-C₅H₁₁ | 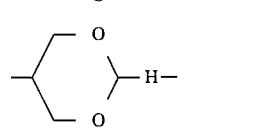 | H | H |
| n-C₅H₁₁ |  | H | F |
| n-C₅H₁₁ | 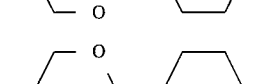 | F | F |

MIXTURE EXAMPLES

Example A

| | | | |
|---|---|---|---|
| PCH-5F | 9.0% | Clearing point [°C.]: | 91.4 |
| PCH-6F | 7.2% | Δn [589 nm, 20° C.]: | 0.1001 |
| PCH-7F | 5.4% | Δε [1 kHz, 20° C.]: | 5.78 |
| CCP-2OCF₃ | 7.2% | ν [mm², s⁻¹]: | 16.10 |
| CCP-3OCF₃ | 10.8% | | |
| CCP-4OCF₃ | 8.1% | | |
| CCP-5OCF₃ | 8.1% | | |
| BCH-3F.F | 10.8% | | |
| BCH-5F.F | 9.0% | | |
| ECCP-3OCF₃ | 4.5% | | |
| ECCP-5OCF₃ | 4.5% | | |
| CBC-33F | 1.8% | | |
| CBC-53F | 1.8% | | |
| CBC-55F | 1.8% | | |
| CPP-5-D1T | 10.0% | | |

Example B

| | | | |
|---|---|---|---|
| PCH-5F | 9.0% | Clearing point [°C.]: | 93 |

-continued

| | | | | |
|---|---|---|---|---|
| PCH-6F | 7.2% | Δn [589 nm, 20° C.]: | 0.0949 |
| PCH-7F | 5.4% | Δε [1 kHz, 20° C.]: | 5.57 |
| CCP-2OCF$_3$ | 7.2% | ν [mm$^2$, s$^{-1}$]: | 16.10 |
| CCP-3OCF$_3$ | 10.8% | | |
| CCP-4OCF$_3$ | 8.1% | | |
| CCP-5OCF$_3$ | 8.1% | | |
| BCH-3F.F | 10.8% | | |
| BCH-5F.F | 9.0% | | |
| ECCP-3OCF$_3$ | 4.5% | | |
| ECCP-5OCF$_3$ | 4.5% | | |
| CBC-33F | 1.8% | | |
| CBC-53F | 1.8% | | |
| CBC-55F | 1.8% | | |
| CCP-5-D1T | 10.0% | | |

We claim:

1. A partially fluorinated benzene compound of formula I

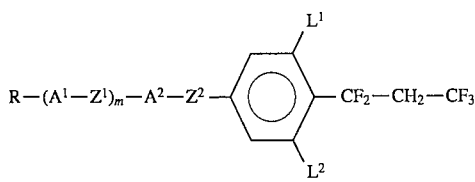

wherein

R is H, alkyl having 1 to 15 carbon atoms which is unsubstituted, monosubstituted by CN or CF$_3$ or at least monosubstituted by halogen, wherein one or more CH$_2$ groups can be replaced, in each case independently of one another by —O—, —S—,

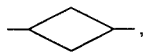

—CO—, —CO—O—, —O—CO— or —O—CO—O—, without O atoms being linked directly to one another, or alkenyl having 1 to 15 carbon atoms which is unsubstituted, monosubstituted by CN or CF$_3$ or at least monosubstituted by halogen, wherein one or more CH$_2$ groups can be replaced, in each case independently of one another, by —O—, —S—,

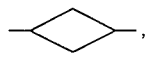

—CO—, —CO—O—, —O—CO— or —O—CO—O—, without O atoms being linked directly to one another;

A$^1$ and A$^2$ are each, independently of one another,
  (a) trans-1,4-cyclohexylene radical in which one or more nonadjacent CH$_2$ groups can each be replaced by —O— or —S—,
  (b) 1,4-phenylene in which one or two CH groups can be replaced by N,
  (c) 1,4-cyclohexenylene, 1,4-bicyclo-(2,2,2)octylene, piperidine-1,4-diyl, naphthalene-2,6-diyl, decahydronaphthalene-2,6-diyl or 1,2,3,4-tetrahydronaphthalene-2,6-diyl, wherein radicals of (a) and (b) can be substituted by one or two fluorine atoms;

Z$^1$ and Z$^2$ are each, independently of one another, —CO—O—, —O—CO—, —CH$_2$O—, —CH$_2$CH$_2$—, —CH=CH—, —C≡C— or a single bond, and one of Z$^1$ and Z$^2$ can also be —(CH$_2$)$_4$— or —CH=CH—CH$_2$CH$_2$—;

m is 0, 1 or 2; and

L$^1$ and L$^2$ are each, independently of one another, H or F.

2. A compound according to claim 1, wherein said compound is of the formula

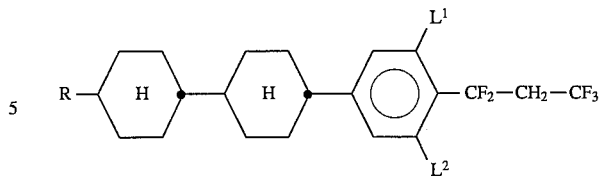

in which R, L$^1$ and L$^2$ are as defined.

3. A compound according to claim 1, wherein said compound is of the formula

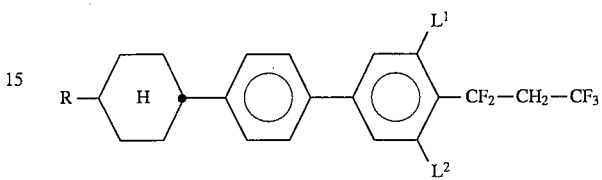

in which R, L$^1$ and L$^2$ are as defined.

4. A compound according to claim 1, wherein said compound is of the formula I6

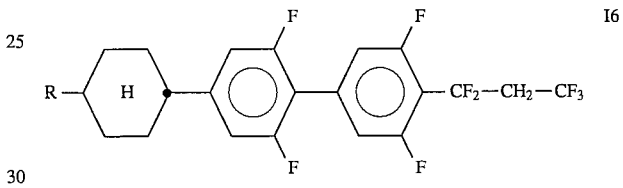

in which R is as defined.

5. A compound according to claim 1, wherein said compound is of the formula I7

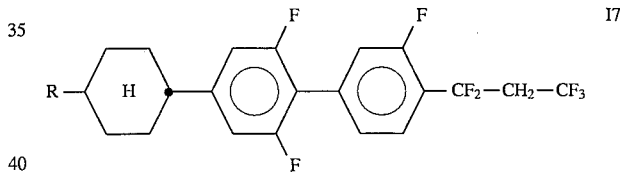

in which R is as defined.

6. A compound according to claim 1, wherein said compound is of the formula I9

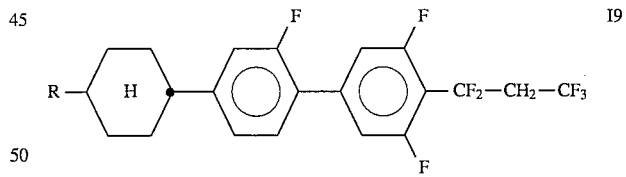

in which R is as defined.

7. In a liquid-crystalline medium having at least two liquid-crystalline compounds, the improvement wherein said medium contains at least one compound according to claim 1.

8. In a liquid-crystal display element containing a liquid-crystalline medium, the improvement wherein said display element contains a medium according to claim 7.

9. In an electrooptical display using a liquid-crystal display element, the improvement wherein said display element contains, as a dielectric, a liquid-crystalline medium according to claim 7.

10. A compound according to claim 1, wherein one of Z$^1$ and Z$^2$ is —(CH$_2$)$_4$— or —CH=CH—CH$_2$CH$_2$— and the other is a single bond.

11. A compound according to claim 1, wherein L$^1$ and L$^2$ are each H.

12. A compound according to claim 1, wherein $L^1$ is F and $L^2$ is H.

13. A compound according to claim 1, wherein $L^1$ and $L^2$ are each F.

14. A compound according to claim 1, wherein said compound is of the formula I12

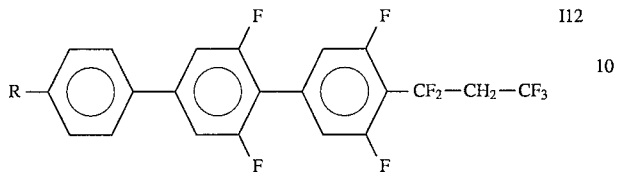

in which R is as defined.

15. A compound according to claim 1, wherein said compound is of the formula I25

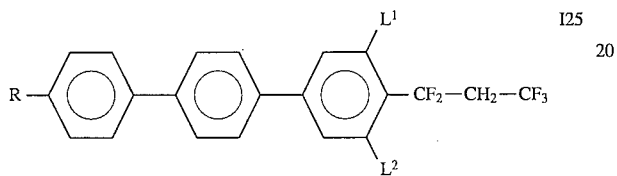

in which R is as defined.

16. A liquid-crystalline medium according to claim 7, wherein said medium contains 1–40 wt. % of compounds of formula I.

17. A liquid-crystalline medium according to claim 7, wherein said medium contains 45–90 wt. % of compounds of formula I.

18. A compound according to claim 1, wherein $A^1$ and $A^2$ are each independently 1,4-cyclohexylene which is unsubstituted or mono- or disubstituted by F or CN, 1,4-cyclohexenylene, 1,4-phenylene which is unsubstituted or mono- or disubstituted by F or CN, pyrimidine-2,5-diyl, pyridine-2,5-diyl or 1,3-dioxane-2,5-diyl;

$Z^1$ and $Z^2$ are each independently a single bond, —CO—O—, —O—CO— or —CH$_2$CH$_2$—; and R is methyl, ethyl, propyl, butyl, pentyl, hexyl, heptyl, octyl, nonyl, decyl, tridecyl, tetradecyl, pentadecyl, methoxy, ethoxy, propoxy, butoxy, pentoxy, heptoxy, octoxy, nonoxy, decoxy, undecoxy, dodecoxy, tridecoxy, tetradecoxy, vinyl, prop-1-enyl, prop-2-enyl, but-1-enyl, but-2-enyl, but-3-enyl, pent-1-enyl, pent-2-enyl, pent-3-enyl, pent-4-enyl, hex-1-enyl, hex-2-enyl, hex-3-enyl, hex-4-enyl, hex-5-enyl, hept-1-enyl, hept-2-enyl, hept-3-enyl, hept-4-enyl, hept-5-enyl, hept-6-enyl, oct-1-enyl, oct-2-enyl, oct-3-enyl, oct-4-enyl, oct-5-enyl, oct-6-enyl, oct-7-enyl, non-1-enyl, non-2-enyl, non-3-enyl, non-4-enyl, non-5-enyl, non-6-enyl, non-7-enyl, non-8-enyl, dec-1-enyl, dec-2-enyl, dec-3-enyl, dec-4-enyl, dec-5-enyl, dec-6-enyl, dec-7-enyl, dec-8-enyl or dec-9-enyl.

\* \* \* \* \*